US009233078B2

(12) United States Patent
Bloom et al.

(10) Patent No.: US 9,233,078 B2
(45) Date of Patent: *Jan. 12, 2016

(54) NANOPARTICLES COMPRISING A NON-IONIZABLE POLYMER AND AN AMINE-FUNCTIONALIZED METHACRYLATE COPOLYMER

(75) Inventors: Corey J. Bloom, Bend, OR (US); Marshall David Crew, Bend, OR (US); Warren Kenyon Miller, Bend, OR (US)

(73) Assignee: Bend Research, Inc., Bend, OR (US)

(*) Notice: Subject to any disclaimer, the term of this patent is extended or adjusted under 35 U.S.C. 154(b) by 621 days.

This patent is subject to a terminal disclaimer.

(21) Appl. No.: 12/746,752

(22) PCT Filed: Dec. 5, 2008

(86) PCT No.: PCT/US2008/013434
§ 371 (c)(1),
(2), (4) Date: Jul. 30, 2010

(87) PCT Pub. No.: WO2009/073216
PCT Pub. Date: Jun. 11, 2009

(65) Prior Publication Data
US 2010/0297237 A1 Nov. 25, 2010

Related U.S. Application Data

(60) Provisional application No. 60/992,804, filed on Dec. 6, 2007.

(51) Int. Cl.
| *A61K 31/47* | (2006.01) |
| *A61K 31/4196* | (2006.01) |
| *A61K 31/5415* | (2006.01) |
| *A61K 9/51* | (2006.01) |
| *A61K 9/00* | (2006.01) |
| *A61K 9/10* | (2006.01) |
| *A61K 9/19* | (2006.01) |

(52) U.S. Cl.
CPC ............. *A61K 9/5138* (2013.01); *A61K 9/0048* (2013.01); *A61K 9/10* (2013.01); *A61K 9/19* (2013.01); *A61K 9/5161* (2013.01); *A61K 9/5192* (2013.01)

(58) Field of Classification Search
CPC ..................................................... A61K 31/42
See application file for complete search history.

(56) References Cited

U.S. PATENT DOCUMENTS

| 3,960,757 A | 6/1976 | Morishita et al. |
| 4,107,288 A | 8/1978 | Oppenheim et al. |
| 4,158,707 A | 6/1979 | Steffen |
| 4,229,360 A | 10/1980 | Schneider |
| 4,298,594 A | 11/1981 | Sears |
| 4,329,332 A | 5/1982 | Couvreur et al. |
| 4,331,654 A | 5/1982 | Morris |
| 4,501,726 A | 2/1985 | Schroder |
| 4,610,868 A | 9/1986 | Fountain et al. |
| 4,615,881 A | 10/1986 | Deibig et al. |
| 4,639,370 A | 1/1987 | Carli |
| 4,649,155 A | 3/1987 | Steffen |
| 4,725,442 A | 2/1988 | Haynes |
| 4,728,513 A | 3/1988 | Ventouras |
| 4,731,210 A | 3/1988 | Weder et al. |
| 4,754,027 A | 6/1988 | Applegren |
| 4,826,689 A | 5/1989 | Violanto |
| 4,830,858 A | 5/1989 | Payne |
| 4,837,381 A | 6/1989 | Steber et al. |
| 4,857,336 A | 8/1989 | Khanna et al. |
| 4,880,634 A | 11/1989 | Speiser |
| 4,882,164 A | 11/1989 | Ferro et al. |
| 4,904,479 A | 2/1990 | Illum |
| 4,917,900 A | 4/1990 | Jones et al. |
| 4,997,454 A | 3/1991 | Violante |
| 5,049,322 A | 9/1991 | Devissaguet et al. |
| 5,051,261 A | 9/1991 | McGinity |
| 5,084,278 A | 1/1992 | Mehta |
| 5,085,864 A | 2/1992 | Cannon et al. |
| 5,091,187 A | 2/1992 | Haynes |
| 5,091,188 A | 2/1992 | Haynes |
| 5,112,621 A | 5/1992 | Stevens et al. |
| 5,118,528 A | 6/1992 | Fessi et al. |
| 5,133,908 A | 7/1992 | Stainmesse et al. |
| 5,145,684 A | 9/1992 | Liversidge et al. |
| 5,152,923 A | 10/1992 | Weder |
| 5,174,930 A | 12/1992 | Stainmesse et al. |
| 5,188,837 A | 2/1993 | Domb |
| 5,202,159 A | 4/1993 | Chen et al. |
| 5,298,262 A | 3/1994 | Na |

(Continued)

FOREIGN PATENT DOCUMENTS

| EP | 877033 A1 | 11/1998 |
| EP | 1180062 B1 | 3/2004 |

(Continued)

OTHER PUBLICATIONS

Al-Kassas, R., "Design and In Vitro Evaluation of Gentamicin-Eudragit Microspheres Intended for Intra-Ocular Administration," Journal of Microencapsulation, 21:1(2004)71-81.
Amrite, A.C., S.P. Ayalasomayajula, and U. Kompella, "Ocular Distribution of Intact Nano- and Micro Particles Following Subconjunctival and Systemic Routes of Administration," Drug Delivery Techn., vol. 2, No. 3, 2003.
Barbu, E., L. Verestiuc, T.G. Nevell, and J. Tsibouldis, "Polymeric Materials for Ophthalmic Drug Delivery: Trends and Perspectives," J. of Materials Chemistry, 16(2006)3439-3443.
Bodmeier et al., "Preparation and Evaluation of Drug-Containing Polymeric Nanosuspensions," presented at the 5th International Conference on Pharmaceutical Technology, Paris, France, 1989. Proceedings vol. 2, pp. 265-268.

(Continued)

*Primary Examiner* — Zohreh Fay
(74) *Attorney, Agent, or Firm* — Klarquist Sparkman, LLP

(57) ABSTRACT

A pharmaceutical composition comprises nanoparticles comprising a poorly water soluble drug, a poorly aqueous soluble non-ionizable polymer, and an amine-functionalized methacrylate copolymer.

16 Claims, 1 Drawing Sheet

(56) References Cited

U.S. PATENT DOCUMENTS

| | | |
|---|---|---|
| 5,302,401 A | 4/1994 | Liversidge et al. |
| 5,314,506 A | 5/1994 | Midler et al. |
| 5,336,507 A | 8/1994 | Na |
| 5,340,591 A | 8/1994 | Nakano et al. |
| 5,352,459 A | 10/1994 | Hollister et al. |
| 5,370,880 A | 12/1994 | Jones et al. |
| 5,445,830 A | 8/1995 | Ishizue et al. |
| 5,456,923 A | 10/1995 | Nakamichi et al. |
| 5,470,583 A | 11/1995 | Na |
| 5,484,608 A | 1/1996 | Rudnic et al. |
| 5,494,683 A | 2/1996 | Liversidge et al. |
| 5,508,276 A | 4/1996 | Anderson et al. |
| 5,510,118 A | 4/1996 | Bosch et al. |
| 5,534,270 A | 7/1996 | De Castro |
| 5,543,158 A | 8/1996 | Gref et al. |
| 5,552,160 A | 9/1996 | Liversidge et al. |
| 5,556,642 A | 9/1996 | Kobayashi et al. |
| 5,560,931 A | 10/1996 | Eickhoff et al. |
| 5,560,932 A | 10/1996 | Bagchi et al. |
| 5,565,188 A | 10/1996 | Wong et al. |
| 5,565,215 A | 10/1996 | Gref et al. |
| 5,569,448 A | 10/1996 | Wong et al. |
| 5,569,469 A | 10/1996 | Lovrecich |
| 5,571,536 A | 11/1996 | Eickhoff et al. |
| 5,573,783 A | 11/1996 | Desieno |
| 5,576,016 A | 11/1996 | Amselem |
| 5,578,325 A | 11/1996 | Domb et al. |
| 5,585,108 A | 12/1996 | Ruddy et al. |
| 5,622,938 A | 4/1997 | Wong |
| 5,662,883 A | 9/1997 | Bagchi et al. |
| 5,662,932 A | 9/1997 | Amselem |
| 5,665,277 A | 9/1997 | Johnson et al. |
| 5,665,331 A | 9/1997 | Bagchi et al. |
| 5,667,800 A | 9/1997 | De Vringer |
| 5,679,690 A | 10/1997 | Andre et al. |
| 5,683,723 A | 11/1997 | Spenlehauer et al. |
| 5,705,196 A | 1/1998 | Galan Valdivia et al. |
| 5,707,634 A | 1/1998 | Schmitt |
| 5,716,642 A | 2/1998 | Bagchi et al. |
| 5,718,919 A | 2/1998 | Ruddy |
| 5,780,062 A | 7/1998 | Frank et al. |
| 5,783,211 A | 7/1998 | Manzo et al. |
| 5,785,976 A | 7/1998 | Westesen |
| 5,834,025 A | 11/1998 | de Garavilla et al. |
| 5,843,509 A | 12/1998 | Calvo Salve et al. |
| 5,853,753 A | 12/1998 | Maierhofer et al. |
| 5,874,111 A | 2/1999 | Maitra et al. |
| 5,885,486 A | 3/1999 | Westesen |
| 5,889,051 A | 3/1999 | Chen et al. |
| 5,919,408 A | 7/1999 | Muller et al. |
| 5,932,249 A | 8/1999 | Gruber et al. |
| 5,935,939 A | 8/1999 | Kararli et al. |
| 5,952,005 A | 9/1999 | Olsson et al. |
| 5,968,551 A | 10/1999 | Oshlack |
| 6,007,845 A | 12/1999 | Domb et al. |
| 6,020,004 A | 2/2000 | Shah |
| 6,027,747 A | 2/2000 | Terracol |
| 6,083,529 A | 7/2000 | Manzo et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee |
| 6,177,103 B1 | 1/2001 | Pace et al. |
| 6,197,348 B1 | 3/2001 | Morella et al. |
| 6,197,349 B1 | 3/2001 | Westesen |
| 6,207,178 B1 | 3/2001 | Westesen |
| 6,217,901 B1 | 4/2001 | Perrott |
| 6,235,224 B1 | 5/2001 | Mathiowitz et al. |
| 6,245,349 B1 | 6/2001 | Yiv et al. |
| 6,254,889 B1 | 7/2001 | Kigoshi et al. |
| 6,267,985 B1 | 7/2001 | Chen |
| 6,267,989 B1 | 7/2001 | Liversidge et al. |
| 6,268,053 B1 | 7/2001 | Woiszwillo et al. |
| 6,270,806 B1 | 8/2001 | Liversidge |
| 6,280,770 B1 | 8/2001 | Pather et al. |
| 6,303,560 B1 | 10/2001 | Hartan et al. |
| 6,361,944 B1 | 3/2002 | Mirkin et al. |
| 6,375,986 B1 | 4/2002 | Ryde |
| 6,383,500 B1 | 5/2002 | Wooley et al. |
| 6,391,338 B1 | 5/2002 | Frisbee et al. |
| 6,406,745 B1 | 6/2002 | Talton |
| 6,428,814 B1 | 8/2002 | Bosch et al. |
| 6,440,458 B1 | 8/2002 | Yamashita et al. |
| 6,443,898 B1 | 9/2002 | Unger et al. |
| 6,447,806 B1 | 9/2002 | Gassmann |
| 6,458,383 B2 | 10/2002 | Chen et al. |
| 6,462,093 B1 | 10/2002 | Miyamoto |
| 6,479,146 B1 | 11/2002 | Caruso et al. |
| 6,485,743 B1 | 11/2002 | Jung et al. |
| 6,509,034 B1 | 1/2003 | Calanchi et al. |
| 6,517,859 B1 | 2/2003 | Tice et al. |
| 6,537,579 B1 | 3/2003 | Desai et al. |
| 6,544,497 B2 | 4/2003 | Zhu et al. |
| 6,548,264 B1 | 4/2003 | Tan et al. |
| 6,551,619 B1 | 4/2003 | Penkler et al. |
| 6,555,139 B2 | 4/2003 | Sharma |
| 6,565,873 B1 | 5/2003 | Shefer |
| 6,565,875 B2 | 5/2003 | Tice et al. |
| 6,565,885 B1 | 5/2003 | Tarara et al. |
| 6,576,264 B1 | 6/2003 | Henriksen et al. |
| 6,579,519 B2 | 6/2003 | Maitra et al. |
| 6,592,899 B2 | 7/2003 | Fowers et al. |
| 6,592,901 B2 | 7/2003 | Durig et al. |
| 6,592,903 B2 | 7/2003 | Ryde |
| 6,596,262 B2 | 7/2003 | Zhu et al. |
| 6,596,311 B1 | 7/2003 | Dobetti |
| 6,607,784 B2 | 8/2003 | Kipp et al. |
| 6,616,869 B2 | 9/2003 | Mathiowitz et al. |
| 6,620,351 B2 | 9/2003 | Gupta |
| 6,623,761 B2 | 9/2003 | Hassan |
| 6,632,671 B2 | 10/2003 | Unger |
| 6,638,537 B2 | 10/2003 | Dennis et al. |
| 6,638,621 B2 | 10/2003 | Anderson |
| 6,638,994 B2 | 10/2003 | Crooks et al. |
| 6,645,517 B2 | 11/2003 | West et al. |
| 6,645,569 B2 | 11/2003 | Cramer et al. |
| 6,649,192 B2 | 11/2003 | Alonso Fernandez et al. |
| 6,652,967 B2 | 11/2003 | Yadav et al. |
| 6,656,504 B1 | 12/2003 | Bosch et al. |
| 6,656,507 B2 | 12/2003 | Petereit et al. |
| 6,656,984 B1 | 12/2003 | Haasmaa et al. |
| 6,660,382 B2 | 12/2003 | Nouri et al. |
| 6,663,885 B1 | 12/2003 | Hager et al. |
| 6,669,959 B1 | 12/2003 | Adjei et al. |
| 6,677,386 B1 | 1/2004 | Giezen et al. |
| 6,682,761 B2 | 1/2004 | Pace |
| 6,682,895 B2 | 1/2004 | Mirkin et al. |
| 6,685,960 B1 | 2/2004 | Gasco |
| 6,692,769 B1 | 2/2004 | Ishibashi et al. |
| 6,696,084 B2 | 2/2004 | Pace et al. |
| 6,709,622 B2 | 3/2004 | Billiet |
| 6,720,008 B2 | 4/2004 | Allison |
| 6,726,934 B1 | 4/2004 | Prokop |
| 6,746,635 B2 | 6/2004 | Mathiowitz et al. |
| 6,755,915 B1 | 6/2004 | Van Soest et al. |
| 6,756,062 B2 | 6/2004 | Johnston et al. |
| 6,761,903 B2 | 7/2004 | Chen et al. |
| 6,780,324 B2 | 8/2004 | Le Garrec et al. |
| 6,793,938 B2 | 9/2004 | Sankaram |
| 6,824,791 B2 | 11/2004 | Mathiowitz et al. |
| 6,827,946 B2 | 12/2004 | Hirsh |
| 6,863,914 B1 | 3/2005 | Auweter et al. |
| 6,869,617 B2 | 3/2005 | Kipp et al. |
| 6,878,693 B2 | 4/2005 | Goldshtein |
| 6,887,493 B2 | 5/2005 | Shefer |
| 6,890,512 B2 | 5/2005 | Roser et al. |
| 7,081,450 B2 | 7/2006 | Goldshtein |
| 7,105,176 B2 | 9/2006 | Auweter et al. |
| 2002/0012675 A1 | 1/2002 | Jain et al. |
| 2002/0054914 A1 | 5/2002 | Morcol |
| 2002/0068092 A1 | 6/2002 | Bosch et al. |
| 2002/0081334 A1 | 6/2002 | Johnston et al. |
| 2002/0106403 A1 | 8/2002 | Parikh et al. |
| 2002/0127278 A1 | 9/2002 | Kipp et al. |

(56) References Cited

U.S. PATENT DOCUMENTS

| | | |
|---|---|---|
| 2002/0142017 A1 | 10/2002 | Simonnet |
| 2002/0169274 A1 | 11/2002 | Eisenberg et al. |
| 2003/0003155 A1 | 1/2003 | Kipp et al. |
| 2003/0026844 A1 | 2/2003 | Lee et al. |
| 2003/0031719 A1 | 2/2003 | Kipp et al. |
| 2003/0049323 A1 | 3/2003 | Hitt et al. |
| 2003/0095928 A1 | 5/2003 | McGurk et al. |
| 2003/0129239 A1 | 7/2003 | Goldshtein |
| 2003/0147965 A1 | 8/2003 | Bassett et al. |
| 2003/0166509 A1 | 9/2003 | Edwards et al. |
| 2003/0170309 A1 | 9/2003 | Babcock et al. |
| 2003/0190347 A1 | 10/2003 | Supersaxo et al. |
| 2003/0206949 A1 | 11/2003 | Parikh et al. |
| 2003/0235619 A1 | 12/2003 | Allen et al. |
| 2004/0009229 A1 | 1/2004 | Unger et al. |
| 2004/0013613 A1 | 1/2004 | Jain et al. |
| 2004/0018229 A1 | 1/2004 | Henriksen et al. |
| 2004/0018236 A1 | 1/2004 | Gurny et al. |
| 2004/0047913 A1 | 3/2004 | Allemann et al. |
| 2004/0067251 A1 | 4/2004 | Johnston et al. |
| 2004/0071776 A1 | 4/2004 | Boudy et al. |
| 2004/0091546 A1 | 5/2004 | Johnson |
| 2004/0180005 A1 | 9/2004 | Jurgens |
| 2004/0191319 A1 | 9/2004 | Yun |
| 2004/0220081 A1 | 11/2004 | Kreitz et al. |
| 2004/0245662 A1 | 12/2004 | Chaubal et al. |
| 2004/0247561 A1 | 12/2004 | Seo et al. |
| 2004/0247624 A1 | 12/2004 | Unger et al. |
| 2004/0265382 A1* | 12/2004 | Kararli et al. .................. 424/469 |
| 2005/0013866 A1 | 1/2005 | Maincent et al. |
| 2005/0025820 A1 | 2/2005 | Kester et al. |
| 2005/0238716 A1 | 10/2005 | Verrijk et al. |
| 2005/0249697 A1 | 11/2005 | Uhrich et al. |
| 2006/0134220 A1 | 6/2006 | Aboubakar et al. |
| 2006/0204577 A1 | 9/2006 | Crew et al. |
| 2006/0240108 A1 | 10/2006 | Bernard |
| 2006/0263434 A1 | 11/2006 | Desai et al. |
| 2007/0026069 A1 | 2/2007 | Shastri et al. |
| 2007/0128289 A1 | 6/2007 | Zhao |
| 2007/0190129 A1 | 8/2007 | Ahmed et al. |
| 2007/0287719 A1 | 12/2007 | Boyden et al. |
| 2010/0183731 A1 | 7/2010 | Miller |
| 2010/0215747 A1 | 8/2010 | Bloom et al. |
| 2010/0266692 A1 | 10/2010 | Bloom et al. |
| 2010/0323014 A1 | 12/2010 | Bloom et al. |

FOREIGN PATENT DOCUMENTS

| | | |
|---|---|---|
| EP | 710261 B1 | 5/2004 |
| WO | WO 9710811 A1 | 3/1997 |
| WO | WO 9713503 A1 | 4/1997 |
| WO | WO 9933558 A1 | 7/1999 |

OTHER PUBLICATIONS

Bodmeier, et al., "Indomethacin Polymer Nanosuspension Prepared by Microfluidization", Journal of Controlled Release, 12 (1990) 223-233.

Bourges, J.-L., S.E. Gautier, F. Delie, R.A. Bejjani, J.-C. Jeanny, R. Gurny, D. BenEzra, and F.F. Behar-Cohen, "Ocular Drug Delivery Targeting the Regina and Retinal Pigment Epithelium Using Polylactide Nanoparticles," Investigative Ophthalmology and Visual Science, 44:8(2003)3562-3569.

Briancon, S., H. fessi, F. Lecomet, and J. Lieto, "Study and Scale-Up of a Nanoprecipitation Process," Industrial Crystallization 1999 (IChemE), pp. 1-10.

Bucolo, C., A. Maltese, F. Maugeri, B. Busa, G. Puglisi, and R. Pignatello, "Eudragit RL100 Nanoparticle System for the Ophthalmic Delivery of Cloricromene," Journal of Pharmacy and Pharmacology, 56(2004)841 846.

Calvo, P., J.L. Vila-Jato, and M.J. Alonso, "Evaluation of Cationic Polymer-Coated Nanocapsules as Ocular Drug Carriers," International Journal of Pharmaceutics, 153(1997)41-50.

Carrasquillo, K.G., J.A. Ricker, I.K. Rigas, J.W. Miller, E.S. Gragoudas, and A.P. Adamis, "Controlled Delivery of the Anti-VEGF Aptamer EYE001 with Poly(lactic-co-glycolic) Acid Microspheres," Investigative Ophthalmology and Visual Science, 44:1(2003)290-299.

Cavalli, R., M.R. Gasco, P. Chetoni, S. Burgalassi, and M.F. Saettone, "Solid Lipid Nanoparticles (SLN) as Ocular Delivery System for Tobramycin," International J. Pharmaceutics, 238(2002)241-245.

Chen et al., "Comparison of Albumin and Casein Microspheres as a Carrier for Doxorubicin," J. Pharm. Pharmacol.39(1987)978-985.

Chiou, W.L., and S.Riegelman, J. Pharm. Sci., 60:9(1971)1281-1302.

Couvreur, Microspheres and Drug Therapy, Elsevier, (1984) pp. 103-115.

De, T.K., D.J. Rodman, B.A. Holm, P.N. Prasad, and E.J. Bergey, "Brimonidine Formulation in Polyacrylic Acid Nanoparticles for Ophthalmic Delivery," J. Microencapsualtion, 20:3)2003)361-374.

Decampos, A.M., A. Sanchez, and M.J. Alonso, "Chitosan Nanoparticles: A New Vehicle for the Improvement of the Delivery of Drugs to the Ocular Surface. Application to Cyclosporin A," International J. of Pharmaceutics, 224(2001)159-168.

Decampos., A.M., A. Sanchez, R. Gref, P. Calvo, and M.J. Alonso, "The Effect of a PGE Versus a Chitosan Coating on the Interaction of Drug Colloidal Carriers with the Ocular Mucosa," European Journal of Pharmaceutical Sciences, 20(2003)73-81.

Dejaeghere, F., E. Allemann, J.-C. Leroux, W. Stevels, J. Feijen, E. Doelker, and R. Gurny, "Formulation of Lyoprotection of Poly(Lactic Acid-Co-Ethylene Oxide) Nanoparticles: Influence on Physical Stability and in Vitro cell Uptake," Pharmaceutical Research, 16:6(1999)859-866.

Desai, S.D., and J. Blanchard, "Pluronic F127-Based Ocular Delivery System Containing Biodegradable Polyisobutylcyanoacrylate Nanocapsules of Pilocarpine," Drug Delivery, 7(2000)201-207.

Fee, C.A., and R.I. Pettigrew, "National Institute of Biomedical Imaging and Bioengineering: Poised for the Future," National Institute of Biomedical Imaging and Bioengineering, 229:3(2003)636-637.

Fessi, H., F. Puisieux, J.Ph. Devissaguet, N. Ammoury, and S. Benita, "Nanocapsule Formation by Interfacial Polymer Deposition Following Solvent Displacement," International J. of Pharmaceutics, 55(1989)R1-R4.

Ford, J.L., Pharm. Acta Helv., 61:3(1986)69-87.

Fox et al., from Proteins in Food Processing, R.Y. Yada (ed), CRC Press, 2004, Chapter 3: The Caseins pp. 29-71.

Gavini, E., P. Chetoni, M. Cossu, M.G. Alvarez, M.F. Saettone, and P. Giunchedi, "PLGA Microspheres for the Ocular Delivery of a Peptide Drug, Vancomycin Using Emulsification/Spray-Drying as the Preparation Method: In Vitro/In Vivo Studies," European Journal of Pharmaceutics and Biopharmaceutics, 57(2004)207-212.

Giannavola, C., C. Bucolo, A. Maltese, D. Paolino, M.A. Vandelli, G. Puglisi, V.H.L. Lee, and M. Fresta, "Influence of Preparation Conditions on Acyclovir-Loaded Poly-d,l-Lactic Acid Nanospheres and Effect of PEG Coating on Ocular Drug Bioavailability." Pharmaceutical Research, 20:4(2003)584-590.

Gurny, Drug Develop. Ind. Pharm. 7(1), 1-25, 1981.

Gurny, R., T. Boye, and H. Ibrahim, "Ocular Therapy with Nanoparticulate Systems for Controlled Drug Delivery," Journal of Controlled Release, 2(1985)353-361.

Harmia, J. Microencapsulation, 1986 vol. 3, No. 1, p. 3-12.

Hasegawa, H., et al., Chem. Pharm. Bull., 33:4(1985)1615-1619; Chem. Pharm. Bull., 34:5(1986)2183-2190; Chem. Pharm. Bull., 36:12(1988) 4941-4950.

Herrero-Vanrell, R., and M.F. Refojo, "Biodegradable Microspheres for Vitreoretinal Drug Delivery," Advanced Drug Delivery Reviews, 52(2001)5 16.

Hornig et al., "Novel Nanoparticles Based on Dextran Esters with Unsaturated Moieties," Macromolecular Rapid Commun., 2005, 26, 1908-1912.

Hornig et al., "Structure Design of Multifunctional Furoate and Pyroglutamate Esters of Dextran by Polymer-Analogous Reactions," Macromol. Biosci. 2007, 7, 297-306.

Hsiue, G.-H., S.-H. Hsu, C.-C. Yang, S.-H. Lee,a nd I.-K. Yang, "Preparation of Controlled Release Ophthalmic Drops, for Glaucoma Therapy Using Thermosensitive poly-N-Isopropylacrylamide," Biomaterials, 23(2002)457 462.

(56) References Cited

OTHER PUBLICATIONS

Kim, S., Y.T. Lim, E.G. Soltesz, A.M. DeGrand, J. Lee, A. Nakayama, J.A. Parker, T. Mihaljevic, R.G. Laurence, D.M. Dor, L.H. Cohn, M.G. Bawendi, and J.V. Frangioni,"Near-Infrared Fluorescent Type II Quantum Dots for Sentinel Lymph Node Mapping," Nature Biotechnology, 22:1(2004)93-97.

Knepp et al., Synthesis, Properties, and Intratumoral Evaluation of Mitoxantrone-Loaded Casein Microspheres in Lewis Lung Carcinoma, J. Pharm. Pharmacol., 45(1993)887-891.

Kompella, U.B., N. Bandi, and S.P. Ayalasomayajula, "Subconjunctival Nano- and Microparticles Sustain Retinal Delivery of Budesonide, A Corticosteroid Capable of Inhibiting VEGF Expression," Investigative Ophthalmology and Visual Science, 44:3(2003)1192-1201.

Kumar, M.N.V., "Nano and Microparticles as Controlled Drug Delivery devices," J. Pharm. Pharmaceutical Sciences, 3:2(2000)234-258.

Latha et al., Casein as a Carrier Matrix for 5-Fluorouracil: Drug Release from Microspheres, Drug-Protein Conjugates and In-Vivo Degradation of Microspheres in Rat Muscle, J. Pharm. Pharmacol., 46(1994)858-862.

Latha et al., Glutaraldehyde Cross-Linked Bovine Casein Microspheres as a Matrix for the Controlled Release of Theophylline: In Vitro Studies, J. Pharm. Pharmacol., 46(1994)8-13.

Latha et al., Progesterone Release from Glutaraldehyde Cross-Linked Casein Microspheres: In Vitro Studies and In Vivo Response in Rabbits, Contraception, 61(2000)329-334.

Lecorre, P., J.H. Rytting, V. Gajan, F. Chevanne, and R. LeVerge, "In Vitro Controlled Release Kinetics of Local Anaesthetics from Poly(D,L-lactice) and Poly (lactice-co-glycolide) Microspheres," Journal of Microencapsulation, 1997, pp. 243-255.

Lellemand, F., O. Felt-Baeyens, K. Besseghir, F. Behar-Cohen, and R. Gurny, "Cyclosporine A Delivery to the Eye: A Pharmaceutical Challenge," European J. of Pharmaceutics and Biopharmaceutics, 56(2003)307 318.

Lemarchand, C., R. Gref, and P. Couvreur, "Polysaccharide-Decorated Nanoparticles," European J. of Pharmaceutics and Biopharmaceutics, 58(204,327-341.

Lemarchand, et al., "Influence of polysaccharide coating on the interactions of nanoparticles with biological systems," Biomaterials, 27(2006)108-118.

Liebert, et al., "Nanoparticles on the Basis of Highly Functionalized Dextrans," J. Am. Chem. Soc. 2005, 127, 10484-10485.

Longmuir, K.J., R.T. Robertson, S.M. Haynes, J.L. Baratta, and A.J. Waring, "Effective Targeting of Liposomes to Liver and Hepatocytes In Vivo by Incorporation of a Plasmodium Amino Acid Sequence," Pharmaceutical Research, 23:4(2006)759-769.

Losa, C., L. Marchal-Heussler, F. Orallo, J.L. Vila Jato, and M.J. Alonso, "Design of New Formulations for Topical Ocular Administration: Polymeric Nanocapsules Containing Metipranolol," Pharmaceutical Research, 10:1(1993)80-87.

Merodio, M., J.M. Irache, F. Valamanesch, and M. Mirshahi, "Ocular Disposition and Tolerance of Ganciclovir-Loaded Albumin Nanoparticles after Intravitreal Injection in Rats," Biomaterials, 23(2002)1587-1594.

Mirshahi et al., Development of Drug Delivery Systems from Vegetal Proteins: Legumin Nanoparticles, Drug Dev. Indust.Pharm., 22:8(1996)841-846.

Mora-Gutierrez et al., Modeling Calcium-Induced Solubility in Caprine Milk Caseins Using a Thermodynamic Linkage Approach, J. Dairy Sci., 76(1993)3698-3710.

Ohio State FST 822 Class Lecture, Casein, 2006, 5 pp.

Pignatello, R., C. Bucolo, and G. Puglisi, "Ocular Tolerability of Eudragit RS100 and RL100 Nanosuspensions as Carriers for Ophthalmic Controlled Drug Delivery," Journal of Pharmaceutical Sciences, 91:12(2002)2636-2641.

Pignatello, R., C. Bucolo, G. Spedalieri, A. Maltese, and G. Puglisi, "Flurbiprofen-Loaded Acrylate Polymer Nanosuspensions for Ophthalmic Application," Biomaterials, 23(2002)3247-3255.

Pignatello, R., C. Bucolo, P. Ferra, A. Maltese, A. Puleo, and G. Puglisi, "Eudragit RS100 Nanosuspensions for the Ophthalmic Controlled Delivery of Ibuprofen," European Journal of Pharmaceutical Sciences, 16(2002)53 61.

Qaddoumi, M.G., H. Ueda, J. Yang, J. Davda, V. Labhasetwar, and V.H.L. Lee, "The Characteristics and Mechanisms of Uptake of PLGA Nanoparticles in Rabbit Conjuctival Epithelial Cell Layers," Pharmaceutical Research, 21:4(2004)641-648.

Raveendran, P, J. Fu, and S.L. Wallen, "Completely 'Green' Synthesis and Stabilization of Metal Nanoparticles," J. American Chemical Society, 125(2003)13940-13941.

Santinho et al., Influence of Formulation on the Physiochemical Properties of Casein Microparticles, Int'l J. Pharm., 186(1999)191-198.

Scholes, P.D., A.G.A. Coombes, L. Ilium, S.S. Savis, M. Vert, and M.C. Davies, "The Preparation of Sub-200 nm Poly(lactide-co-glycolide) Microspheres for Site-Specific Drug Delivery," J. Controlled Release, 25(1993)145-153.

Sjostrom, et al., Journal of Pharmaceutical Sciences, vol. 82, No. 6 Jun. 1993, pp. 584-589.

Sugimoto, I., K. Sasaki, A. Kuchiki, T. Ishihara, and H. Nakagawa, Chem. Pharm. Bull, 30:12(1982)4479-4488.

Suverkrup, R., S. Grunthal, O. Krasichkova, S. Maier, A. Weischselbaum, B. Neff, M. Diestelhorst, S. Dinslage, and A. Lux, "The Ophthalmic Lyophilisate Carrier System (OLCS): Development of a Novel Dosage Form, Freeze-Drying Technique, and In Vitro Quality Control Tests," European J. Pharmaceutics and Biopharmaceutics, 57(2004)269-277.

Takayama, K., N. Nambu, and T. Nagai., Chem. Pharm. Bull., 30:2(1982)673-678.

Takenaka, H., Y. Kawashima and S.Y. Lin, J. Pharm. Sci., 69:12(1980)1388-1392.

Takeuchi, H., T. Handa and Y. Kawashima, Chem. Pharm. Bull., 35:9(1987)3800-3806.

Tuovinen, L., E. Ruhanen, T. Kinnarinen, S. Ronkko, J. Pelkonen, A. Urtti, S. Peltonen, and K. Jarvinen, "Starch Acetate Microparticles for Drug Delivery Into Retinal Pigment Epithelium—In Vitro Study," J. of Controlled Release, 98(2004)407-413.

Ueda, M., A. Iwara, and J. Kreuter, "Influence of the Preparation Methods on the Drug Release Behaviour of Loperamide-Loaded Nanoparticles," J. Microencapsulation, 15:3(1998)361-372.

University of Guelph, Dairy Chemistry and Physics, 2006, 16 pp.

Vandamme, Th.F., "Microemulsions as Ocular Drug Delivery Systems: Recent Developments and Future Challenges," Progress in Retinal and Eye Research, 21(2002)15-34.

Vandervoort, J., and A. Ludwig, "Preparation and Evaluation of Drug-Loaded Gelatin Nanoparticles for Topical Ophthalmic Use," European J. of Pharmaceutics and Biopharmaceutics, 57(2004)251-261.

Willmott et al., Doxorubicin-Loaded Casein Microspheres: Protean Nature of Drug Incorporation J. Pharm. Pharmacol. 42(1992)472-475.

Zahr, A.S., M. de Villiers, and M.V. Pishko, "Encapsulation of Drug Nanoparticles in Self-Assembled Macromolecular Nanoshells," Langmuir, 21(2005)503 410.

Zimmer, A., and J. Kreuter, "Microspheres and Nanoparticles Used in Ocular Delivery Systems," Advanced Drug Delivery Reviews, 16(1995)61-73.

Aliabadi, H.M. et al., "Micelles of methoxy poly(ethylene oxide)-b-poly(ε-caprolactone as vehicles for the solubilization and controlled delivery of cyclosporine A," *Journal of Controlled Release*, vol. 104, No. 2, pp. 301-311 (May 2005).

Celikkaya, E. et al., "Rifampicin carrying poly (D,L-lactide)/poly-(ethylene glycol) microspheres: loading and release," *Artificial Organs, Blackwell Scientific Publications,* vol. 20, No. 7, pp. 743-751 (Jul. 1996).

Hsieh Ming-Fa et al.m "Nano-sized micelles of block copolymers of methoxy poly(ethylene glycol)-poly(epsilon-caprolactone)-graft-2-hydroxyethyl cellulose for doxorubicin delivery" *Journal of*

(56) References Cited

OTHER PUBLICATIONS

*Nanoscience and Nanotechnology,* vol. 8, No. 5, pp. 2362-2368 (May 2008).

Liggins, et al., "Solid-State Characterization of Paclitaxel," *Journal of Pharmaceutical Sciences,* vol. 86, No. 12, pp. 1458-1463 (Dec. 1997).

Mu, L., et al., "Vitamin E TPGS used as emulsifier in the solvent evaporation/extraction technique for fabrication of polymeric nanosphers for controlled release of paclitaxel (Taxol<(>R))," *Journal of Controlled Release,* vol. 80., No. 1-3, pp. 129-144 (Apr. 2002).

Shuai et al., "Core-Cross-Linked Polymeric Micelles as Paclitaxel Carriers," *Bioconjug. Chem.,* vol. 15, No. 3, pp. 441-448 (May 2004).

Shuai, X. et al., "Micellar carriers based on block copolymers of poly(epsilon-caprolactone) and poly(ethylene glycol) for doxorubicin delivery" *Journal of Controlled Release,* vol. 98, No. 3, pp. 415-426 (Aug. 2004).

\* cited by examiner

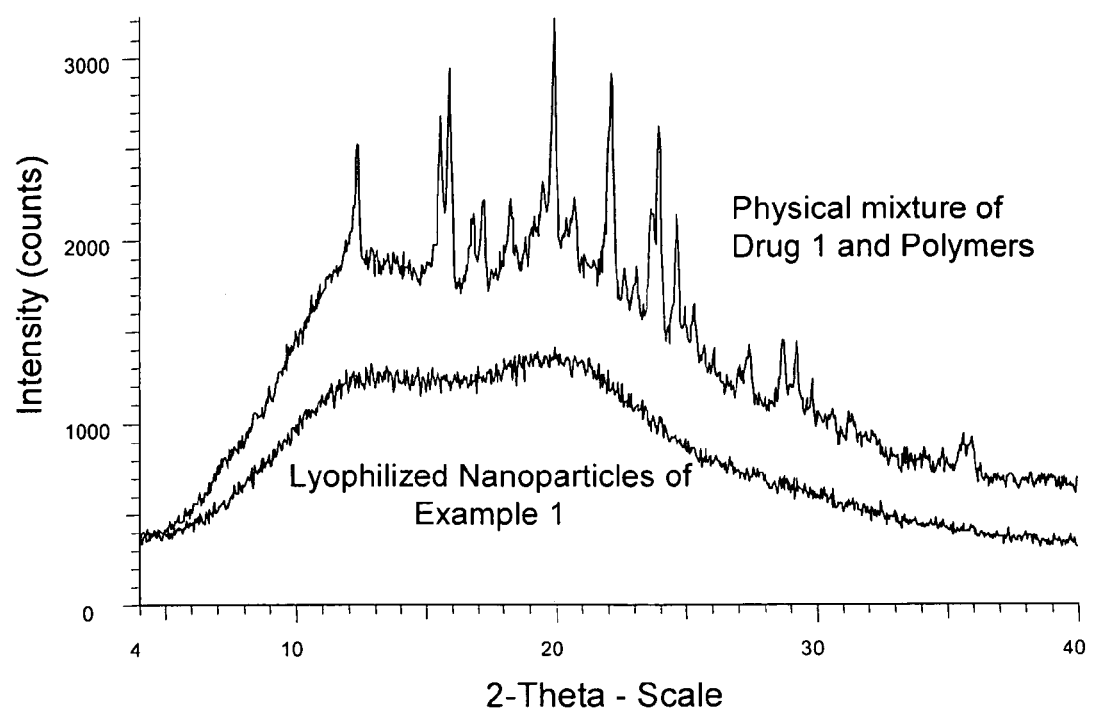

NANOPARTICLES COMPRISING A NON-IONIZABLE POLYMER AND AN AMINE-FUNCTIONALIZED METHACRYLATE COPOLYMER

This is a 371 of PCT/US2008/013434 filed Dec. 5, 2008 and claims priority of U.S. Application No. 60/992,804 filed Dec. 6, 2007.

BACKGROUND OF THE INVENTION

The present invention relates to nanoparticles comprising a poorly water-soluble drug, a poorly aqueous soluble non-ionizable polymer and an amine-functionalized methacrylate copolymer.

A variety of approaches have been taken to formulate drugs as nanoparticles. One approach is to decrease the size of crystalline drug by grinding or milling the drug in the presence of a surface modifier. See, e.g., U.S. Pat. No. 5,145,684. Another approach to forming nanoparticles is to precipitate the drug in the presence of a film forming material such as a polymer. See, e.g., U.S. Pat. No. 5,118,528.

Amine-functionalized methacrylate copolymers, such as Eudragit RL100® and Eudragit RS100® have been used in nanoparticle compositions. See, for example, Bucolo et al., *J. Pharmacy and Pharmacology*, 2004, 56, 841-846; Pignatello et al., *J. Pharm. Sci.*, 2002, Vol. 91, No. 12, 2636-2641; and Rabinovich-Guilatt, et al., *J. Drug Targeting*, 2004, Vol. 12 (9-10), 623-633. Nanoparticles of a polymer and a positively charged polysaccharide have also been made, with a therapeutic substance associated with the nanoparticle. See, for example, US Published Patent Application 2006/0134220.

Alonso Fernandez et al., U.S. Pat. No. 6,649,192 B2 disclose nanoparticles for the administration of macromolecules comprising a combination of hydrophilic polymers. The polymers are chitosan (an aminopolysaccharide) or its derivatives and optionally polyoxyethylene or its derivatives.

Shefer et al., U.S. Pat. No. 6,565,873 B1 disclose nanoparticles having an average particle diameter of from about 20 nm to about 10 microns, which comprise a biodegradable solid hydrophobic core and a bioadhesive/mucoadhesive positively charged surfactant that is entrapped and fixed to the particle surface. The nanoparticles are for delivery to an oral cavity or mucous membranes.

Maincent et al., US Pub. Patent Application 2005/0013866 A1 disclose particulate vectors for increasing the absorption of actives comprising at least one biodegradable polymer combined with at least one polycationic polymer. The particulate vectors may be nanoparticles.

Aboubakar, et al. US Published Patent Application 2006/0134220 disclose nanoparticles of a polymer and a positively charged polysaccharide. The drug is adsorbed to the nanoparticle.

BRIEF SUMMARY OF THE INVENTION

In a first aspect, a pharmaceutical composition comprises nanoparticles, the nanoparticles comprising: (a) a poorly water soluble drug having a solubility in water of less than 5 mg/mL over the pH range of 6.5 to 7.5 at 25° C., at least 90 wt % of the drug in the nanoparticles being non-crystalline; (b) a poorly water soluble non-ionizable polymer; and (c) an amine-functionalized methacrylate copolymer; wherein the nanoparticles have an average size of less than 500 nm; and the drug, the non-ionizable polymer, and the amine-functionalized methacrylate copolymer collectively constitute at least 80 wt % of the nanoparticles.

In one embodiment, the poorly water soluble non-ionizable polymer is selected from the group consisting of ethylcellulose, cellulose acetate, cellulose propionate, cellulose butyrate, cellulose acetate butyrate, and mixtures thereof.

In another embodiment, the amine-functionalized methacrylate copolymer is poly[ethylacrylate-co-methyl methacrylate-co-trimethylamonioethyl methacrylate chloride].

There is also provided a method for treating a disorder of the eye by administering a therapeutically effective amount of the compositions of the present invention.

In yet another embodiment, the non-ionizable polymer is selected from the group consisting of ethylcellulose, cellulose acetate, cellulose propionate, cellulose butyrate, cellulose acetate butyrate, and mixtures thereof, and the amine-functionalized methacrylate copolymer is poly [ethylacrylate-co-methyl methacrylate-co-trimethylamonioethyl methacrylate chloride].

In still another embodiment, the non-ionizable polymer is ethylcellulose and the amine-functionalized methacrylate copolymer is poly[ethylacrylate-co-methyl methacrylate-co-trimethylamonioethyl methacrylate chloride].

Nanoparticles comprising a poorly water soluble drug, a poorly aqueous soluble non-ionizable polymer, and an amine-functionalized methacrylate copolymer result in a material that improves exposure of the drug to target tissue when administered to an in vivo aqueous use environment.

Because the nanoparticles are formed from a blend of a poorly aqueous soluble non-ionizable polymer and an amine-functionalized methacrylate copolymer, the stability of the non-crystalline drug and the suspension stability of the nanoparticle can be addressed independently, resulting in nanoparticles with improved performance and stability.

First, the poorly aqueous soluble non-ionizable polymer used in the nanoparticles stabilizes the poorly water soluble drug in the sense of reducing the rate of crystallization of the drug in the solid state and while in suspension in vivo. The non-ionizable polymer is chosen so that a portion of the drug is soluble in the polymer. This helps prevent or reduce the rate of crystallization of the non-crystalline drug in the nanoparticle. In addition, because the non-ionizable polymer is poorly aqueous soluble at physiological pH, the nanoparticles maintain the drug within a solid (or at least undissolved) polymer matrix when the nanoparticles are suspended in an aqueous solution, further preventing or reducing crystallization of the drug. It is well known that the non-crystalline form of a low-solubility drug provides a greater aqueous concentration of drug relative to the crystalline form of the drug when administered to an aqueous use environment. However, it is also well known that when the drug is not stabilized in the non-crystalline form, the drug rapidly converts to the crystalline form in the use environment. See, for example, Hancock and Parks (*Pharmaceutical Research*, Vol. 17, No. 4, 2000). Thus, the poorly aqueous soluble non-ionizable polymer is selected to maintain the stability of non-crystalline drug in the nanoparticle and while suspended in an aqueous solution, resulting in an enhanced concentration of free drug when the nanoparticle is administered to an aqueous use environment.

Second, the amine-functionalized methacrylate copolymer provides a charge when the nanoparticles are suspended in an aqueous use environment, thus reducing or eliminating agglomeration of the nanoparticles. In addition, an amine-functionalized methacrylate copolymer results in improved mucoadhesion of the nanoparticles when used in vivo. The amine-functionalized methacrylate copolymer also results in improved re-suspendability of solid compositions containing nanoparticles relative to surfactant-based and neutral polymer-based stabilizers: solid compositions of the invention resuspend nanoparticles when administered to an aqueous solution.

Finally, the nanoparticles may provide improved toleration relative to conventional nanoparticles that incorporate a substantial amount of surfactant to stabilize the nanoparticles.

The combination of the two different polymers—the non-ionizable polymer and the amine-functionalized methacrylate copolymer—provides a synergistic effect that cannot be obtained when using only one polymeric species, resulting in improved stability and re-suspendability of the nanoparticles.

The foregoing and other objectives, features, and advantages of the invention will be more readily understood upon consideration of the following detailed description of the invention.

BRIEF DESCRIPTION OF THE SEVERAL VIEWS OF THE DRAWINGS

FIG. 1 is a powder X ray diffraction (PXRD) diffractogram of the lyophilized nanoparticles of Example 1.

DETAILED DESCRIPTION OF THE INVENTION

The nanoparticles of the present invention comprise a poorly water soluble drug, a poorly aqueous soluble non-ionizable polymer, and an amine-functionalized methacrylate copolymer. At least 90 wt % of the drug in the nanoparticle is non-crystalline. The nature of the nanoparticles, suitable amine-functionalized methacrylate copolymers and drugs, and methods for making nanoparticles are described in detail below.

Nanoparticles

The nanoparticles comprise the drug, the non-ionizable polymer and the amine-functionalized methacrylate copolymer. By "nanoparticles" is meant a plurality of small particles in which the average size of the particles is less than about 500 nm. In suspension, by "average size" is meant the effective cumulant diameter as measured by dynamic light scattering (DLS), using for example, Brookhaven Instruments' 90Plus particle sizing instrument. By "size" is meant the diameter if the particles were spherical particles, or the maximum diameter for non-spherical particles. Preferably, the average size of the nanoparticles is less than 400 nm, more preferably less 300 nm, and most preferably less than 200 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," Applied Optics, 40(24), 4087-4091 (2001) for a discussion of cumulant diameter and polydispersity. Preferably, the polydispersity of the nanoparticles is less than 0.5. More preferably, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

At least 90 wt % of the drug in the nanoparticles is non-crystalline. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. As previously discussed, the non-crystalline form of a low-solubility drug is preferred as it provides a greater aqueous concentration of drug relative to the crystalline form of the drug in an aqueous use environment. Preferably at least about 95 wt % of the drug in the nanoparticle is non-crystalline; in other words, the amount of drug in crystalline form does not exceed about 5 wt %. Amounts of crystalline drug may be measured by Powder X-Ray Diffraction (PXRD), by Differential Scanning Calorimetry (DSC), by solid state nuclear magnetic resonance (NMR), or by any other known quantitative measurement.

The nanoparticles can exist in a number of different configurations. In one embodiment, the nanoparticles comprise a core, the core comprising the non-crystalline drug and the poorly aqueous soluble non-ionizable polymer. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, fourier transform infra red (FTIR) analysis, and raman spectroscopy; (3) chromatographic techniques, such as high performance liquid chromatography (HPLC), and gel-permeation chromatography (GPC); and (4) other techniques known in the art.

In one embodiment, the non-crystalline drug and the poorly aqueous soluble non-ionizable polymer constitute at least 60 wt % of the core, more preferably at least 80 wt % of the core. In another embodiment, the core consists essentially of the non-crystalline drug and the poorly aqueous soluble non-ionizable polymer.

The non-crystalline drug present in the core can exist in non-crystalline pure drug domains, as a thermodynamically stable solid solution of non-crystalline drug homogeneously distributed throughout the non-ionizable polymer, as a supersaturated solid solution of non-crystalline drug homogeneously distributed throughout the non-ionizable polymer, or any combination of these states or those states that lie between them. When the glass-transition temperature ($T_g$) of the non-crystalline drug is different from the $T_g$ of the pure polymer by at least about 20° C., the core may exhibit a $T_g$ that is different from the $T_g$ of pure non-crystalline drug or pure polymer. Preferably, less than 20 wt % of the drug is present in non-crystalline drug domains, with the remaining drug homogeneously distributed throughout the non-ionizable polymer.

In yet another embodiment, the core comprises the non-crystalline drug, the poorly aqueous soluble non-ionizable polymer, and an amine-functionalized methacrylate copolymer. In this embodiment, the drug, non-ionizable polymer, and amine-functionalized methacrylate copolymer constitute at least 60 wt % of the core, more preferably at least 80 wt % of the core.

The core may be (1) a homogeneous molecular mixture of drug, non-ionizable polymer, and amine-functionalized methacrylate copolymer, (2) domains of pure drug, domains of pure non-ionizable polymer, and domains of pure amine-functionalized methacrylate copolymer distributed throughout the core, or (3) any combination of these states or those states that lie between them. In one embodiment, the drug, non-ionizable polymer, and amine-functionalized methacrylate copolymer are homogeneously distributed throughout the core as a supersaturated solid solution. In another embodiment, the surface portion of the nanoparticle has a higher concentration of amine-functionalized methacrylate copolymer relative to the nanoparticle as a whole.

In still another embodiment, the core comprises the non-crystalline drug and the poorly aqueous soluble non-ionizable polymer, with the amine-functionalized methacrylate copolymer adsorbed to the surface portion of the nanoparticle.

In yet another embodiment, the core comprises the non-crystalline drug, the poorly aqueous soluble non-ionizable polymer, and a portion of the amine-functionalized methacrylate copolymer. The remaining portion of the amine-functionalized methacrylate copolymer is adsorbed to the surface portion of the nanoparticle. In this embodiment, a portion of the amine-functionalized methacrylate copolymer is integral to the core, while the remaining portion of amine-functionalized methacrylate copolymer is adsorbed to the surface portion of the nanoparticle.

The drug and polymers are collectively present in the nanoparticle in an amount ranging from about 80 wt % to 100 wt %. Preferably, the drug and polymers collectively constitute at least 85 wt %, more preferably at least 90 wt % of the nanoparticle. In one embodiment, the nanoparticles consist essentially of the drug, the non-ionizable polymer and the amine-functionalized methacrylate copolymer. By "consist essentially of" is meant that the nanoparticle contains less than 1 wt % of any other excipients and that any such excipients have substantially no affect on the performance or properties of the nanoparticle.

The amount of drug in the nanoparticle may range from 0.1 wt % to 90 wt %. Preferably the amount of drug in the nanoparticle ranges from about 1 wt % to about 80 wt %, more preferably from about 5 wt % to about 75 wt %, even more preferably from about 10 wt % to about 60 wt %, and most preferably from about 10 wt % to about 50 wt %.

To minimize the total mass of the formulation, high drug loadings are desired. However, if the amount of drug in the nanoparticle is too high, the nanoparticles suspension becomes unstable, resulting in crystallization of the drug in the suspension. Additionally, large amounts of drug in the nanoparticle can lead to crystalline drug formation when the nanoparticles are isolated from suspension in solid form. In absolute terms, it is generally preferred that the amount of drug in the nanoparticle be less than about 90 wt %, more preferably less than about 80 wt %, even more preferably less than about 75 wt % the total mass of the nanoparticle.

The amount of poorly aqueous soluble non-ionizable polymer may range from 10 wt % to 75 wt %. Preferably, the amount of poorly aqueous soluble non-ionizable polymer ranges from 20 wt % to 60 wt %, and more preferably from 25 wt % to 60 wt %. The physical stability of the non-crystalline drug in the nanoparticle tends to improve with increasing amounts of the poorly aqueous soluble non-ionizable polymer. Accordingly, it is preferred that the amount of poorly aqueous soluble non-ionizable polymer in the nanoparticle is at least 15 wt %, more preferably at least 20 wt %, and most preferably at least 25 wt %. However, too much non-ionizable polymer will lead to low drug loading in the nanoparticle and low amounts of the amine-functionalized methacrylate copolymer. Thus, it is preferred that the amount of poorly aqueous soluble non-ionizable polymer in the nanoparticle is 70% or less, and most preferably 60 wt % or less.

The amount of amine-functionalized methacrylate copolymer may range from 5 wt % to 80 wt %, preferably from 10 wt % to 70 wt %, and more preferably from 20 wt % to 50 wt %. Preferably, the amine-functionalized methacrylate copolymer is present in a sufficient amount so that the nanoparticles have sufficient surface charge so that they do not agglomerate into larger particles in solution. Preferably the amount of amine-functionalized methacrylate copolymer in the nanoparticle is at least 10 wt %, more preferably at least 15 wt %, and most preferably at least 20 wt %. However, too much amine-functionalized methacrylate copolymer will lead to low drug loading and low amounts of the non-ionizable polymer. Thus, it is preferred that the amount of amine-functionalized methacrylate copolymer be 75 wt % or less, more preferably 70 wt % or less, even more preferably 60 wt % or less, and most preferably 50 wt % or less.

In one embodiment, the mass ratio of non-ionizable polymer to amine-functionalized methacrylate copolymer ranges from 1:8 to 15:1, more preferably from 1:6 to 9:1, even more preferably from 1:4 to 4:1, and most preferably from 1:3 to 3:1.

Preferably, there is a sufficient amount of non-ionizable polymer to stabilize the drug in the nanoparticle, and a sufficient amount of amine-functionalized methacrylate copolymer to stabilize the nanoparticles in solution.

Preferred embodiments of nanoparticles have the following amount of drug, poorly aqueous soluble non-ionizable polymer and amine-functionalized methacrylate copolymer:

5 to 75 wt %, preferably 10 to 60 wt % drug;

10 to 75 wt %, preferably 20 to 60 wt % poorly aqueous soluble non-ionizable polymer; and 5 to 60 wt %, preferably 20 to 50 wt % amine-functionalized methacrylate copolymer.

The nanoparticle is preferably substantially free from surfactants. By a "surfactant" is meant a surface-active material with a molecular weight of less than about 2000 daltons having a hydrophobic portion and a hydrophilic portion, and which is soluble in the use environment. By substantially "free from" is meant that the amount of surfactant present in the composition is less than 0.1 wt %. Preferably, the amount of the surfactant present in the nanoparticles is less than the detection limit.

Preferably, the nanoparticles are ionized when present in an aqueous use environment. It is believed that physical stability of the nanoparticles, in the sense of not aggregating or flocculating, is related, in part, to the amount of electric charge on the nanoparticle. An indirect measure of charge is zeta potential. The nanoparticles preferably have a zeta potential of greater than +10 mV. Preferably, to reduce aggregation, the zeta potential is at least +20 mV, more preferably at least +30 mV, and even more preferably at least +40 mV. Zeta potential is typically calculated from the electrophoretic mobility measured by light scattering, R. J. Hunter, *Zeta Potential in Colloid Science. Principles and Applications*, Academic Press, 1981. Zeta potential may be measured using any number of commercially-available instruments, such as Brookhaven Instruments Corp. (Holtsville, N.Y.) ZetaPals zeta potential analyzer.

Non-Ionizable Polymers

The nanoparticles of the present invention comprise a poorly aqueous soluble non-ionizable polymer. The term "polymer" is used conventionally, meaning a compound that is made of monomers connected together to form a larger molecule. A polymer generally consists of at least about 20 monomers connected together. Thus, the molecular weight of the polymer generally will be about 2000 daltons or more. The polymer should be inert, in the sense that it does not chemically react with the drug in an adverse manner, and should be pharmaceutically acceptable.

The polymer is a poorly aqueous soluble non-ionizable polymer. By "poorly aqueous soluble" is meant that the polymer has a solubility of less than 0.1 mg/mL when administered alone at a concentration of 0.2 mg/mL to a phosphate buffered saline solution (PBS) at pH 6.5. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. A test to determine whether the polymer is poorly aqueous soluble may be performed as follows. The polymer is initially present in bulk powder form with average particle sizes of greater than about 1 micron. The polymer alone is administered at a concentration of 0.2 mg/mL to the PBS solution and stirred for approximately 1 hour at room temperature. Next, a nylon 0.45 μm filter is weighed, and the polymer solution is filtered. The filter is dried overnight at 40° C., and weighed the following morning. The amount of polymer dissolved is calculated from the amount of polymer added to the PBS solution minus the amount of polymer remaining on the filter (mg). The non-ionizable polymer is considered to be poorly aqueous soluble if it has a solubility of less than 0.1 mg/mL in this test. Preferably, when administered at a concentration of 0.2 mg/mL to the pH 6.5 PBS, a poorly aqueous soluble non-ionizable polymer has a solubility of less than 0.07 mg/mL, more preferably less than 0.05 mg/mL, and most preferably less than 0.01 mg/mL.

To ease processing, it is preferred that the poorly aqueous soluble non-ionizable polymer be soluble in an organic solvent. Preferably the polymer has a solubility in an organic solvent of at least about 0.1 mg/mL, and preferably at least 1 mg/mL. Preferably the polymer is not crosslinked.

The polymer is "non-ionizable," meaning that the polymer possesses substantially no ionizable functional groups. By "substantially no ionizable functional groups" is meant that the number of ionizable groups covalently attached to the polymer is less than about 0.05 milliequivalents per gram of polymer. Preferably, the number is less than about 0.02 milliequivalents per gram of polymer. By "ionizable groups" is meant functional groups that are at least about 10% ionized over at least a portion of the physiologically relevant pH range of 1 to 8. Such groups have $pK_a$ values of about 0 to 9.

Poorly aqueous soluble non-ionizable polymers for use with the present invention include substituted cellulosics, and non-cellulosics. By "cellulosic" is meant a cellulose polymer that has been modified by reaction of at least a portion of the hydroxyl groups on the saccharide repeating units with a compound to form an ester or an ether substituent.

In order to be poorly aqueous soluble, the polymer preferably has a sufficient number of hydrophobic groups relative to hydrophilic groups. In a preferred embodiment, the poorly aqueous soluble non-ionizable cellulosic has an ether- or ester-linked alkyl substituent. Suitable alkyl substituents include $C_1$ to $C_4$ alkyl groups. Exemplary ether-linked alkyl substituents include methyl, ethyl, propyl, and butyl groups. Exemplary ester-linked alkyl substituents include acetate, propionate, and butyrate groups.

Exemplary substituted cellulosics include methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, and hydroxypropyl methylcellulose butyrate. Preferably the poorly aqueous soluble non-ionizable polymer is selected from the group consisting of ethyl cellulose, cellulose acetate, cellulose propionate, cellulose butyrate, and cellulose acetate butyrate.

Exemplary non-cellulosics include vinyl polymers and copolymers, such as poly(vinyl acetate), poly(vinyl acetate-co-vinyl alcohol), and poly(ethylene-co-vinyl acetate); polymethacrylate and polyacrylate polymers and copolymers, such as poly(ethyl acrylate-co-methyl methacrylate), available as EUDRAGIT® NE; polylactones, such as poly(lactide), poly(glycolide), poly(ε-caprolactone), and copolymers of these, including poly(lactide-co-glycolide), poly(lactide-co-ε-caprolactone), poly(ethylene oxide-co-ε-caprolactone), poly(ethylene oxide-co-lactide), and poly(ethylene oxide-co-lactide-co-glycolide); and poly(alkyl)cyanoacrylates, such as poly(isobutyl)cyanoacrylate, and poly(hexyl)cyanoacrylate; and mixtures thereof.

In one embodiment, the non-ionizable polymer is selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(vinyl acetate), poly(vinyl acetate-co-vinyl alcohol), poly(ethylene-co-vinyl acetate), poly(ethyl acrylate-co-methyl methacrylate) (available as EUDRAGIT® NE), poly(lactide), poly(glycolide), poly(ε-caprolactone), poly(lactide-co-glycolide), poly(lactide-co-ε-caprolactone), poly(ethylene oxide-co-ε-caprolactone), poly(ethylene oxide-co-lactide), poly(ethylene oxide-co-lactide-co-glycolide, poly(isobutyl)cyanoacrylate, and poly(hexyl)cyanoacrylate.

In another embodiment, the non-ionizable polymer is selected from the group consisting of ethylcellulose, cellulose acetate, cellulose propionate, cellulose butyrate, and cellulose acetate butyrate.

In another embodiment, the non-ionizable polymer is ethylcellulose.

Amine-Functionalized Methacrylate Copolymers

The nanoparticles also comprise an amine-functionalized methacrylate copolymer. By "amine-functionalized" is meant that the methacrylate copolymer has at least one amine group. The amine group can be either a primary amine, a secondary amine, a tertiary amine, or a quaternary amine. By "methacrylate copolymer" is meant that the copolymer is made by polymerization of at least two methacrylate or acrylate monomers. In a preferred embodiment, at least one of the methacrylate monomers is amine functionalized.

Exemplary amine-functionalized methacrylate copolymers include EUDRAGIT® RL (poly[ethylacrylate-co-methyl methacrylate-co-trimethylamonioethyl methacrylate chloride] having a 1:2:0.2 monomer ratio), EUDRAGIT® RS (poly[ethylacrylate-co-methyl methacrylate-co-trimethylamonioethyl methacrylate chloride] having a 1:2:0.1 monomer ratio) manufactured by Rohm Tech Inc., EUDRAGIT® E (poly[butyl methacrylate-co-{2-dimethylaminomethyl methacrylate}-co-methylmethacrylate] with a 1:2:1 monomer ratio), also manufactured by Rohm Tech Inc. and mixtures thereof.

In one embodiment, the polymer is a poorly aqueous soluble amine-functionalized methacrylate polymer. By "poorly aqueous soluble" is meant that the polymer has a solubility of less than 0.1 mg/mL when administered alone at a concentration of 0.2 mg/mL to a phosphate buffered saline solution (PBS) at pH 6.5, as previously described. Preferably, a poorly aqueous soluble polymer has a solubility of less than 0.07 mg/mL, more preferably less than 0.05 mg/mL, and most preferably less than 0.01 mg/mL.

In one embodiment, the amine-functionalized methacrylate copolymer is poly[ethylacrylate-co-methyl methacrylate-co-trimethylamonioethyl methacrylate chloride].

In yet another embodiment, the non-ionizable polymer is selected from the group consisting of methylcellulose ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, hydroxypropyl methylcellulose acetate, low-substituted hydroxypropyl methylcellulose, hydroxypropyl methylcellulose propionate, hydroxypropyl methylcellulose butyrate, poly(vinyl acetate), poly(vinyl acetate-co-vinyl alcohol), poly(ethylene-co-vinyl acetate), poly(ethyl acrylate-co-methyl methacrylate), poly(lactide), poly(glycolide), poly($\epsilon$-caprolactone), poly(lactide-co-glycolide), poly(lactide-co-$\epsilon$-caprolactone), poly(ethylene oxide-co-$\epsilon$-caprolactone), poly(ethylene oxide-co-lactide), poly(ethylene oxide-co-lactide-co-glycolide, poly(isobutyl) cyanoacrylate, and poly(hexyl)cyanoacrylate, and the amine-functionalized methacrylate copolymer is poly[ethylacrylate-co-methyl methacrylate-co-trimethylamonioethyl methacrylate chloride.

In still another embodiment, the non-ionizable polymer is selected from the group consisting of ethylcellulose, cellulose acetate, cellulose propionate, cellulose butyrate, and cellulose acetate butyrate, and the amine-functionalized methacrylate copolymer is poly[ethylacrylate-co-methyl methacrylate-co-trimethylamonioethyl methacrylate chloride].

In yet another embodiment, the non-ionizable polymer is ethylcellulose, and the amine-functionalized methacrylate copolymer is poly[ethylacrylate-co-methyl methacrylate-co-trimethylamonioethyl methacrylate chloride].

The Drug

The drug is a "poorly water soluble drug," meaning that the drug has a solubility in water (over the pH range of 6.5 to 7.5 at 25° C.) of less than 5 mg/mL. The utility of the invention increases as the water solubility of the drug decreases. The drug may have an even lower aqueous solubility, such as less than about 1 mg/mL, less than about 0.1 mg/mL, and even less than about 0.01 mg/mL.

In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, compounds for use in the following therapeutic areas: antihypertensives, antianxiety agents, antiarrythmia agents, anti-clotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, anti-obesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Each named drug should be understood to include the nonionized form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Exemplary drugs suitable for use in the nanoparticles include, but are not limited to, phosphodiesterase inhibitors, such as sildenafil and sildenafil citrate; HMG-CoA reductase inhibitors, such as atorvastatin, lovastatin, simvastatin, pravastatin, fluvastatin, rosuvastatin, itavastatin, nisvastatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; calcium channel blockers, such as nifedipine, nicardipine, verapamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; carbonic anhydrase inhibitors; and glycogen phosphorylase inhibitors. Other low-solubility drugs suitable for use in the nanoparticles are disclosed in US Published patent application 2005/0031692, herein incorporated by reference.

In another embodiment, the drug is a hydrophobic non-ionizable drug. By "hydrophobic non-ionizable drug" is meant a subclass of non-ionizable drugs that are essentially water insoluble and highly hydrophobic, and are characterized by a set of physical properties, as described hereinafter. By "non-ionizable" is meant that the drug has substantially no ionizable groups. By "ionizable groups" is meant functional groups that are at least about 10% ionized over at least a portion of the physiologically relevant pH range of 1 to 8. Such groups have pKa values of about 0 to 9. Thus, hydrophobic non-ionizable drugs do not have a pKa value between 0 and 9.

The first property of hydrophobic drugs is that they are extremely hydrophobic. Log P, defined as the base 10 logarithm of the ratio of the drug solubility in octanol to the drug solubility in water, is a widely accepted measure of hydrophobicity. By "extremely hydrophobic" is meant that the Log P value of the drug is at least 4.0, preferably at least 4.5, and most preferably at least 5.0. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J. Chem. Inf. Comput. Sci. 21 (1987)); Viswanadhan's fragmentation method (29 J. Chem. Inf. Comput. Sci. 163 (1989)); or Broto's fragmentation method (19 Eur. J. Med. Chem.-Chim. Theor. 71 (1984). Preferably the Log P value is calculated by using the average value estimated using Crippen's, Viswanadhan's, and Broto's fragmentation methods.

The second property of hydrophobic drugs is that they have an extremely low solubility in water over the pH range of 6.5 to 7.5 at 25° C. By "extremely low solubility in water" is meant that the solubility of the drug in water is less than 100 µg/mL. Preferably, the hydrophobic drug has a water solubility of less than 50 µg/mL, and most preferably less than 10 µg/mL.

Exemplary drugs having these properties include cholesteryl ester transfer protein inhibitors (CETPIs), such as (2R)-3-[[3-(4-chloro-3-ethylphenoxy)phenyl]][[3-(1,1,2,2-tetrafluoroethoxy)phenyl]methyl]amino]-1,1,1-trifluoro-2-propanol; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; and pharmaceutically acceptable forms thereof.

In one embodiment, the drug is suitable for topical administration to the eye. The compositions may be useful in the treatment of glaucoma or ocular hypertension, age related macular degeneration, diabetic retinopathy, macular oedema, dry eye, bacterial infections, fungal infections and inflammation. Exemplary drugs suitable for ocular administration include beta-blockers, such as timolol, betaxolol, and levobunolol; carbonic anhydrase inhibitors, such as brinzolamide and dorzolamide; prostaglandins such as latanoprost and travoprost; adrenergic agonists including clonidine derivatives, such as apraclonidine or brimonidine; cytotoxic chemotherapeutic agents, such as taxol, taxotere, vinblastine, cis-platin, doxorubicin, and adriamycin; vascular endothelial growth factor inhibitors such as sunitinib, sorafenib, axitinib, and pazopanib; other anti-angiogenic agents, such as combretastatin A-4, endostatin, prinomastat, celecoxib, and rofocoxib; anti-inflammatory compounds such as dexamethasone; anti-virals such as ganciclovir and fomivirsen; antiinbacterials such as levofloxacin and moxifloxacin.

Process for Making Nanoparticles

The nanoparticles may be formed by any process that results in formation of nanoparticles of non-crystalline drug, a non-ionizable polymer, and an amine-functionalized methacrylate copolymer. The drug used to form the nanoparticles may be in a crystalline or non-crystalline form; however, at least 90 wt % of the drug in the resulting nanoparticles is in non-crystalline form.

One process for forming nanoparticles is an emulsification process. In this process, the drug and polymer are dissolved in an organic solvent that is immiscible with an aqueous solution in which drug and polymers are poorly soluble, forming an organic solution. Solvents suitable for forming the solution of dissolved drug and polymers can be any compound or mixture of compounds in which the drug and the polymer are mutually soluble and which is immiscible with the aqueous solution. As used herein, the term "immiscible" means that the organic solvent has a solubility in the aqueous solution of less than about 10 wt %, preferably less than about 5 wt %, and most preferably less than about 3 wt %. Preferably, the solvent is also volatile with a boiling point of 150° C. or less. Exemplary organic solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. Preferred organic solvents are methylene chloride, ethyl acetate, benzyl alcohol, and mixtures thereof. The aqueous solution is preferably water.

Once the organic solution is formed, it is then mixed with the aqueous solution and homogenized to form an emulsion of fine droplets of the water immiscible solvent distributed throughout the aqueous phase. The volume ratio of organic solution to aqueous solution used in the process will generally range from 1:100 (organic solution:aqueous solution) to 2:3 (organic solution:aqueous solution). Preferably, the organic solution:aqueous solution volume ratio ranges from 1:9 to 1:2 (organic solution:aqueous solution). The emulsion is generally formed by a two-step homogenization procedure. The solution of drug, polymer and organic solvent are first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. Preferably, the organic solvent is removed to a level that is acceptable according to The International Committee on Harmonization (ICH) guidelines. Preferably, the concentration of organic solvent in the nanoparticle suspension is less than the solubility of the organic solvent in the aqueous solution. Even lower concentrations of organic solvent are preferred. Thus, the concentration of organic solvent in the nanoparticle suspension may be less than about 5 wt %, less than about 3 wt %, less than 1 wt %, and even less than 0.1 wt %.

Alternatively, the drug and non-ionizable polymer are dissolved in an organic solvent that is immiscible with the aqueous solution, while the amine-functionalized methacrylate copolymer is dissolved or suspended in the aqueous solution. The nanoparticles are then formed using the above emulsification procedure.

An alternative process to form the nanoparticles is a precipitation process. In this process, the drug and polymers are first dissolved in an organic solvent that is miscible with an aqueous solution in which the drug and polymers are poorly soluble. The resulting organic solution is mixed with the aqueous solution causing the nanoparticles to precipitate. Solvents suitable for forming the solution of dissolved drug and polymers can be any compound or mixture of compounds in which the drug and the polymer are mutually soluble and which is miscible in the aqueous solution. Preferably, the organic solvent is also volatile with a boiling point of 150° C. or less. Exemplary solvents include acetone, methanol, ethanol, tetrahydrofuran (THF), and dimethylsulfoxide (DMSO). Mixtures of solvents, such as 50% methanol and 50% acetone, can also be used, so long as the polymer and drug are sufficiently soluble to dissolve the drug and polymer. Preferred solvents are methanol, acetone, and mixtures thereof.

The aqueous solution may be any compound or mixture of compounds in which the drug and polymers are sufficiently insoluble so as to precipitate to form nanoparticles. The aqueous solution is preferably water.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

Alternatively, the drug and non-ionizable polymer are dissolved in the organic solvent, while the amine-functionalized methacrylate copolymer is dissolved or suspended in the aqueous solution. The nanoparticles are then formed using the above precipitation procedure.

For the precipitation process, the amount of drug and polymers in the organic solution depends on the solubility of each in the organic solvent and the desired ratios of drug to polymers in the resulting nanoparticles. The organic solution may comprise from about 0.1 wt % to about 20 wt % dissolved solids. A dissolved solids content of from about 0.5 wt % to 10 wt % is preferred.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). Preferably, the organic solution:aqueous solution volume ratio ranges from about 1:20 to about 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. Preferably, the solvent is removed to a level that is acceptable according to ICH guidelines. Thus, the concentration of solvent in the nanoparticle suspension may be less than about 10 wt %, less than about 5 wt %, less than about 3 wt %, less than 1 wt %, and even less than 0.1 wt %.

Thus, in one embodiment, a process for forming nanoparticles, comprises: (a) forming an organic solution comprising a poorly water soluble drug and a poorly aqueous soluble non-ionizable polymer dissolved in an organic solvent, wherein the drug has a solubility in water of less than 5 mg/ml over the pH range of 6.5 to 7.5; (b) forming an aqueous solution, wherein the drug and the non-ionizable polymer are poorly soluble in the aqueous solution; (c) adding an amine-functionalized methacrylate copolymer to at least one of the organic solution and the aqueous solution; (d) mixing the organic solution with the aqueous solution to form a first mixture; (e) removing the solvent from the first mixture to form a suspension comprising the nanoparticles and the aqueous solution, wherein (i) the nanoparticles have an average size of less than 500 nm, (ii) at least 90 wt % of the drug in the nanoparticles is non-crystalline, and (iii) the drug, the non-ionizable polymer, and the amine-functionalized methacrylate copolymer collectively constitute at least 80 wt % of the nanoparticles.

Both the emulsion process and the precipitation process result in the formation of a suspension of the nanoparticles in the aqueous solution. In some instances it is desirable to concentrate the nanoparticles or to isolate the nanoparticles in solid form by removing some or all of the liquid from the suspension. Exemplary processes for removing at least a portion of the liquid include spray drying, spray coating, spray layering, lyophylization, evaporation, vacuum evaporation, filtration, ultrafiltration, reverse osmosis, and other processes known in the art. Preferably, the liquid is removed by a process selected from spray drying, evaporation, and lyophylization. In one embodiment, the liquid is removed by spray drying. In another embodiment, the liquid is removed by evaporation. In still another embodiment, the liquid is removed by lyophylization. In yet another embodiment, the liquid is removed by a combination of processes selected from the group consisting of spray drying, spray coating, spray layering, lyophylization, evaporation, vacuum evaporation, filtration, ultrafiltration, and reverse osmosis. For example, a portion of the liquids may be removed by filtration to concentrate the nanoparticles, followed by spray-drying to remove most of the remaining liquids, followed by a further drying step such as tray-drying.

When isolating the nanoparticles in solid form, it is often desirable to include a matrix material in the suspension of nanoparticles prior to removal of the liquids. The matrix material functions to help slow or prevent agglomeration of the nanoparticles as the liquids are being removed, as well as to help re-suspend the nanoparticles when the solid composition is added to an aqueous solution (e.g., an aqueous environment of use). The matrix material is preferably pharmaceutically acceptable and water soluble. Examples of matrix materials include polyvinyl pyrrolidone (PVP), trehalose, hydroxypropyl methyl cellulose (HPMC), hydroxypropyl cellulose (HPC), casein, caseinate, albumin, gelatin, acacia, lactose, mannitol, pharmaceutically acceptable forms thereof, and other matrix materials know in the art.

In one embodiment of the invention, a solid composition comprises (a) a plurality of nanoparticles comprising a poorly water-soluble drug, a non-ionizable polymer, and an amine-functionalized methacrylate copolymer, and (b) a matrix material. As used herein, the term "solid pharmaceutical composition" means that the composition is in a solid form and substantially free of liquids. The nanoparticles are entrapped or encapsulated in the matrix material.

The presence of nanoparticles in the solid composition can be determined using the following procedure. A sample of the solid composition is embedded in a suitable material, such as an epoxy or polyacrylic acid (e.g., LR White from London Resin Co., London, England). The sample is then microtomed to obtain a cross-section of the solid composition that is about 100 to 200 nm thick. This sample is then analyzed using transmission electron microscopy (TEM) with energy dispersive X-ray (EDX) analysis. TEM-EDX analysis quantitatively measures the concentration and type of atoms larger than boron over the surface of the sample. From this analysis, regions that are rich in drug can be distinguished from regions that are rich in the matrix material. The size of the regions that are rich in drug will have an average diameter of less than 500 nm in this analysis, demonstrating that the solid composition comprises nanoparticles of drug in the matrix material. See, for example, *Transmission Electron Microscopy and Diffractometry of Materials* (2001) for further details of the TEM-EDX method.

Another procedure that demonstrates the solid composition contains nanoparticles is to administer a sample of the solid composition to water to form a suspension of the nanoparticles. The suspension is then analyzed by DLS as described herein. A solid composition of the invention will form nanoparticles having an average cumulant diameter of less than 500 nm.

A specific procedure for demonstrating the solid composition contains nanoparticles is as follows. A sample of the solid composition is added to water at ambient temperature such that the concentration of solids is less than about 1 mg/mL. The so-formed suspension is then analyzed by DLS. The solid composition contains nanoparticles if the DLS analysis results in particles having an average cumulant diameter of less than 500 nm.

A solid composition of the invention will show the presence of nanoparticles in at least one, and preferably both of the above tests.

Resuspendability

In one embodiment, solid compositions of the present invention result in improved resuspendability of the nanoparticles relative to surfactant-based stabilizers. The term "resuspendability" as used herein means the ability of the solid material, when administered to an aqueous use environment, to form a nanoparticle suspension.

The ability of the solid composition to resuspend nanoparticles when administered to an aqueous solution can be determined using the following procedures. In the first procedure, the average particle size of the re-suspended material is determined as follows. The solid composition is added to an aqueous solution, such as water, PBS, or a model fasted duodenal (MFD) solution, to form a suspension. A sample of the solid composition is added to water at ambient temperature such that the concentration of solids is less than about 1 mg/mL. The average particle size of the nanoparticles formed during this (re)suspension is then determined by DLS techniques. A solid composition is said to provide good resuspendability if, upon administration to an aqueous solution, the average particle size as determined by DLS techniques is at least 50% and no more than 200% the average particle size of the nanoparticles prior to recovery of the solid composition. Preferably, the formulation provides an average particle size that is at least 67% and no more than 150% the average particle size prior to recovery of the solid composition. Even more preferably, the formulation provides an average particle size that is at least 75% and no more than 133% the average particle size prior to recovery of the solid composition.

The second procedure is known as a filter potency test. In this test the concentration of drug after passing the suspension of the nanoparticles through a filter is determined. The solid composition is added to an aqueous solution as described above. The concentration of drug in the so-formed suspension is then determined using standard techniques, such as by high-performance liquid chromatography (HPLC). Next, the suspension is filtered through a filter, and the concentration of drug in the filtered sample is determined via standard techniques. A loss in potency after filtering a sample through a filter is an indication that the nanoparticles in the sample are larger than the filter pore size. Exemplary filters that can be used in this test include a 1-μm glass fiber filter, a 0.45-μm syringe filter, and a 0.2-μm syringe filter. One skilled in the art will understand that the pore size of the filter should be selected to ensure the nanoparticles are not retained on the filter. Generally, the pore size of filter and the range of nanoparticle average diameters are given as follows:

| Filter Pore Size (μm) | Suitable Range of Nanoparticle Diameters (nm) |
|---|---|
| 1 | >250 |
| 0.45 | 150 to 300 |
| 0.2 | <200 |

A solid composition is said to provide good resuspendability if the ratio of the concentration of drug in the filtered sample is at least 60% the concentration of drug in the unfiltered sample. Preferably, the concentration of drug in the filtered sample is at least 70% the concentration of drug in the unfiltered sample. Most preferably, the concentration of drug in the filtered sample is at least 80% the concentration of drug in the unfiltered sample.

In an especially preferred embodiment, a composition provides good resuspendability in both of the tests described above.

Dosage Forms

The compositions of the present invention may be administered using any known dosage form. The nanoparticles may be formulated for administration via oral, topical, subdermal, intranasal, buccal, intrathecal, ocular, intraaural, intraarticular, subcutaneous spaces, vaginal tract, arterial and venous blood vessels, pulmonary tract or intramuscular tissue of an animal, such as a mammal and particularly a human. Oral dosage forms include: powders or granules; tablets; chewable tablets; capsules; unit dose packets, sometimes referred to in the art as "sachets" or "oral powders for constitution" (OPC); syrups; and suspensions. Parenteral dosage forms include reconstitutable powders or suspensions. Topical dosage forms include creams, pastes, suspensions, powders, foams and gels. Ocular dosage forms include suspensions, emulsions, powders, gels, creams, pastes, solid inserts, depots, and implants.

In one embodiment, the dosage form comprises an isotonic suspension of nanoparticles, or powder that can be resuspended to provide such a suspension. The suspension may be administered topically to the eye, such as with eye drops, to treat a disorder of the eye.

In one embodiment, the compositions of the present invention are capable of improving the concentration of dissolved drug in a use environment relative to a control composition consisting essentially of the drug alone without any of the polymers. In order to determine concentration enhancement in vitro, the amount of "free" drug, or solvated drug is measured. By "free" drug is meant drug which is in the form of dissolved drug or present in micelles, but which is not in the nanoparticles or any solid particles larger than 500 nm, such as precipitate. A composition of the invention provides concentration enhancement if, when administered to an aqueous use environment, it provides a free drug concentration that is at least 1.25-fold the free drug concentration provided by the control composition. Preferably, the free drug concentration provided by the compositions of the invention are at least about 1.5-fold, more preferably at least about 2-fold, and most preferably at least about 3-fold that provided by the control composition.

Alternatively, the compositions of the present invention, when dosed orally to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when dosed orally to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

In another embodiment, the compositions provide higher concentrations of the drug in ocular tissues and fluids, including the iris-ciliary body (ICB), tear film, choroid, retina, cornea, aqueous vitreous humor, and aqueous humor relative to the control composition when the compositions are administered to the eye. The compositions of the present invention provide a concentration of the drug in the ICB that is at least 1.25 fold relative to the control composition, more preferably by at least 2 fold, and even more preferably by at least 3 fold. Alternatively, the compositions of the present invention provide a concentration of the drug in the aqueous humor that is at least 1.25 fold relative to the control composition, more preferably by at least 2 fold, and even more preferably by at least 3 fold.

In another embodiment, the compositions provide relatively higher concentrations of the drug in intraocular tissue for sustained periods of time when the compositions are administered to the eye. The compositions of the present invention provide an ICB AUC that is at least 1.25 fold relative to the control composition, more preferably by at least 2 fold, and even more preferably by at least 3 fold. Alternatively, the compositions of the present invention provide an aqueous humor AUC that is at least 1.25 fold relative to the control composition, more preferably by at least 2 fold, and even more preferably by at least 3 fold.

In vivo determinations of in vivo concentrations of the drug in the ICB and aqueous humor may be determined in appropriate model animals, such as rabbits.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

EXAMPLES

Drugs Used in Examples

The following drugs were used in the examples as described below.

Drug 1 was 4-(5-methyl-3-phenyl-4-isoxazolyl) benzenesulfonamide, also known as valdecoxib, having the structure:

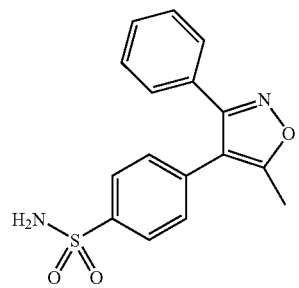 [SMILES: Cc1onc(-c2ccccc2)c1-c1ccc(S(N)(=O)=O)cc1]

Drug 1 has a solubility in water of about 10 μg/mL, and a Log P value of about 3.0. The $T_g$ of non-crystalline Drug 1 was determined by DSC analysis to be 55° C., while the $T_m$ of crystalline Drug 1 was 170° C.

Drug 2 was [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, having the structure:

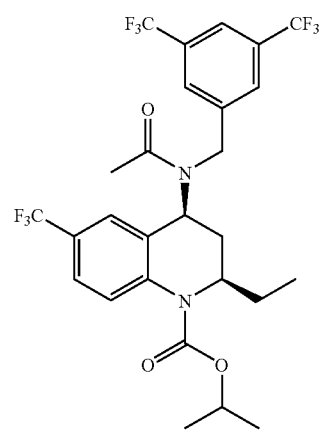 [SMILES: CC[C@@H]1C[C@H](N(Cc2cc(C(F)(F)F)cc(C(F)(F)F)c2)C(C)=O)c2cc(C(F)(F)F)ccc2N1C(=O)OC(C)C]

Drug 2 has a solubility in water of less than 1 μg/mL, and a Log P value of 6.7, as determined by the average value estimated using Crippen's, Viswanadhan's, and Broto's fragmentation methods. The $T_g$ of non-crystalline Drug 2 was determined by DSC analysis to be 46° C.

Drug 3 has the structure:

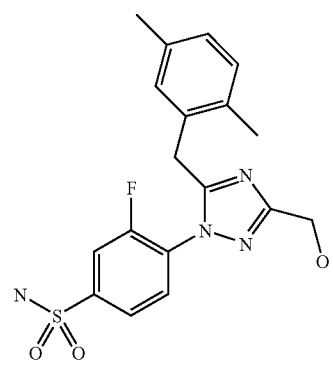 [SMILES: Cc1ccc(C)c(Cc2nc(CO)nn2-c2ccc(S(N)(=O)=O)cc2F)c1]

Drug 3 has an aqueous solubility of about 650 µg/mL, and a CLogP value of 1.9.

Drug 4 has the structure:

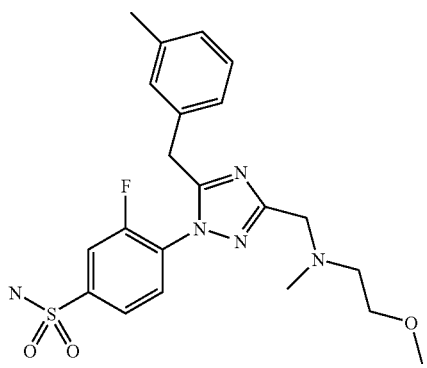 [SMILES: COCCN(C)Cc1nc(Cc2cccc(C)c2)n(-c2ccc(S(N)(=O)=O)cc2F)n1]

Drug 4 has an aqueous solubility of about 740 µg/mL, and a CLogP value of 2.3.

Drug 5 was brinzolamide, having the structure:

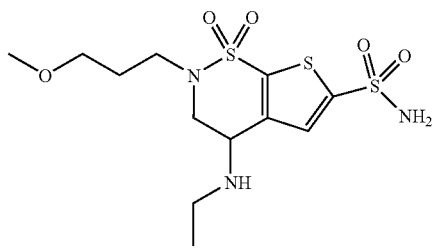 [SMILES: CCNC1CN(CCCOC)S(=O)(=O)c2sc(S(N)(=O)=O)cc21]

Drug 5 has an aqueous solubility of about 490 µg/mL, and a CLogP value of 0.33.

Polymers Used in Examples

The following poorly aqueous soluble non-ionizable polymers were used in the examples: ethylcellulose (ETHOCEL® Viscosity 4, Dow Chemical Co., Midland, Mich.); cellulose triacetate (CA-435-75S, available from Eastman Chem. Co., Kingsport, Tenn.); cellulose acetate butyrate (CAB-551-0.01, available from Eastman Chem. Co.).

These polymers were evaluated using the following procedure to verify that they are poorly aqueous soluble. First, 0.2 mg/mL of the polymer was added to a PBS solution consisting of 20 mM $Na_2HPO_4$, 47 mM $KH_2PO_4$, 87 mM NaCl, and 0.2 mM KCl, adjusted to pH 6.5 with NaOH. The polymer was stirred in the PBS solution for approximately 1 hour at room temperature. Next, the polymer solution was filtered through a nylon 0.45 µm filter that was weighed dry prior to filtration. The filter was dried overnight at 40° C., and weighed the following morning. The amount of soluble polymer was calculated from the amount of polymer added to form the polymer solution minus the amount of polymer remaining on the filter. The results of these tests are shown in Table 1 and show that all of the polymers tested are poorly aqueous soluble.

TABLE 1

| Example Polymer | Amount Soluble at pH 6.5 (mg/mL) | Observations |
| --- | --- | --- |
| Ethylcellulose | <0.001 | Fine particle suspension |
| Cellulose Triacetate | <0.001 | Fine particle suspension |
| Cellulose Acetate Butyrate | 0.01 | Fine particle suspension |
| Eudragit RL PO | 0.04 | Fine particle suspension |

The amine-functionalized methacrylate copolymer used in the examples was Eudragit RL PO (poly[ethylacrylate-methyl methacrylate-trimethylamonioethyl methacrylate chloride] monomer ratio of 1:2:0.2, available from Röhm America, Piscataway, N.J.).

The aqueous solubility of this polymer was determined using the above procedure, and the results are reported in Table 1.

Example 1

Nanoparticles containing valdecoxib ("Drug 1") were prepared as follows. First, 74.4 mg valdecoxib, 77.9 mg of the poorly aqueous soluble non-ionizable polymer ethylcellulose (ETHOCEL viscosity 4, available from Dow Chemical Co., Midland, Mich.), and 158.9 mg of the amine-functionalized methacrylate copolymer Eudragit RL PO (available from Röhm America, Piscataway, N.J.) were dissolved in 19.91 g methylene chloride to form an organic solution. This organic solution was then poured into 20 mL of deionized water and emulsified for 5 min using a Kinematica Polytron 3100 rotor/stator (Kinematica AG, Lucerne, Switzerland) at 10,000 rpm. The solution was further emulsified using a microfluidizer (Microfluidics [Newton, Mass.] model M-110L F12Y with Z chamber), with an inlet pressure of 70 psi for 5 minutes. The methylene chloride was then removed from the emulsion using a rotary evaporator (28° C., 200 rpm, 20 min), resulting in an aqueous suspension of nanoparticles.

Light Scattering Analysis

The particle size of the nanoparticles in the aqueous suspension was determined using DLS as follows. First, the aqueous suspension was filtered using a 1 µm glass membrane filter (Anatop filter, Whatman), and poured into a cuvette. Dynamic light-scattering was measured using a Brookhaven Instruments (Holtsville, N.Y.) BI-200SM particle size analyzer with a BI-9000AT correlator. The sums of exponentials from the autocorrelation functions were analyzed using CONTIN software to extract size distributions from the samples. The cumulant diameter of the nanoparticles of Example 1 was found to be 178 nm, with a polydispersity of 0.19.

Isolation of Solid Nanoparticles

The nanoparticles of Example 1 were isolated in solid form using the following procedure. First, 200 mg polyvinyl pyrrolidone (PVP, Kollidon 12 PF, available from BASF Corp., Mount Olive, N.J.) was added to 10 mL of the aqueous suspension of nanoparticles. The solution was filtered using a 1 µm glass membrane filter, then lyophilized overnight to obtain a dry powder.

Powder X-Ray Diffraction Analysis

The lyophilized nanoparticles of Example 1 were examined using powder x-ray diffraction (PXRD) with a Bruker AXS D8 Advance diffractometer to determine the non-crystalline character of the drug in the nanoparticles. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The x-ray source ($KCu_\alpha$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 40°. A physical mixture of crystalline Drug 1, ethylcellulose, and EUDRAGIT® RL PO was also analyzed using the same procedure for comparison. The results are shown in FIG. 1. The lyophilized nanoparticles of Example 1 exhibited a diffraction pattern showing only an amorphous halo, while a physical mixture of crystalline Drug 1 and the two polymers exhibited a pattern showing sharp peaks characteristic of crystalline drug. These data indicate that essentially all of the drug in the nanoparticles of Example 1 is non-crystalline.

Resuspension of Solid Nanoparticles

The lyophilized nanoparticles were resuspended in deionized water at two concentrations. A sufficient quantity of lyophilized nanoparticles was added to 1 mL of deionized water, to obtain resuspension potencies of about 2.5 mgA/mL and 10 mgA/mL, respectively. The suspensions were vortexed 10 seconds, then sonicated for 10 minutes. Next, 100 μL of each aqueous nanoparticle suspension was added to 2 mL deionized water in a cuvette, and particle size was analyzed using DLS as described above. The cumulant diameter of the resuspended nanoparticles was found to be 181 nm with a polydispersity of 0.19 for the 2.5 mgA/mL sample, and 179 nm with a polydispersity of 0.19 for the 10 mgA/mL sample. This demonstrates that a small particle size can be maintained after isolation of the nanoparticles in dry powder form, followed by resuspension.

The resuspensions were allowed to stand unmixed for 2 hours (ambient conditions) to measure stability. DLS analysis showed that the cumulant diameter of the resuspended nanoparticles after 2 hours was 168 nm with a polydispersity of 0.22 for the 2.5 mgA/mL sample, and 177 nm with a polydispersity of 0.23 for the 10 mgA/mL sample. These results demonstrate that the nanoparticle suspensions are stable for at least two hours with no significant particle agglomeration.

Free Drug Analysis

The amount of free drug provided by a suspension of the nanoparticles of Example 1 was measured using the following procedure. A 2.5 mgA/mL nanoparticle suspension was formed by adding 1 mL deionized water to approximately 39 mg lyophilized nanoparticles and approximately 50 mg solid dextrose, to yield a suspension with an osmolarity of about 300 mOsm. The suspension was filtered using a centrifuge tube filter with a 100,000-dalton molecular-weight cutoff. The filtrate solution was assayed by high-performance liquid chromatography (HPLC). As shown in Table 2, the nanoparticles of Example 1 provided a free drug concentration that was 3.1-fold that provided by bulk crystalline valdecoxib.

TABLE 2

| Sample | Free Drug (μg/mL) |
|---|---|
| Bulk valdecoxib | 11 |
| Nanoparticles of Example 1 | 36 |

Example 2

The nanoparticles of Example 2 were prepared as follows. First, 100.5 mg Drug 1, 151.4 mg ethylcellulose, and 151.1 mg Eudragit RL were dissolved in 20 mL methylene chloride to form an organic solution. The organic solution was then poured into the 80 mL deionized water and emulsified for 5 min using a Kinematica Polytron 3100 rotor/stator at 10,000 rpm. The solution was further emulsified using a microfluidizer with an inlet pressure of 76 psi for 25 minutes. The methylene chloride was removed from the emulsion using a rotary evaporator (room temperature, 200 rpm, 7 min), resulting in an aqueous suspension of nanoparticles.

Light Scattering Analysis

The aqueous suspension of nanoparticles was filtered using a 1 μm glass membrane filter, diluted 1:10, and analyzed using DLS as described above. The cumulant diameter of the nanoparticles in aqueous suspension was 126 nm, with a polydispersity of 0.22.

The aqueous suspension was allowed to stand unmixed for 6 weeks (ambient conditions) to measure stability. DLS analysis showed that the cumulant diameter of the nanoparticle suspension after 6 weeks was 94 nm, with a polydispersity of 0.10. These results demonstrate that the nanoparticle suspensions are stable for at least 6 weeks with no measurable particle agglomeration.

Control 1

As a control, nanoparticles were prepared containing Drug 1 and the amine-functionalized methacrylate copolymer Eudragit RL, but with no poorly aqueous soluble non-ionizable polymer. To form the Control 1 nanoparticles, the organic solution consisted of 21.4 mg Drug 1 and 57.9 mg Eudragit RL dissolved in 6 mL methylene chloride. The organic solution was then poured into 20 mL deionized water and emulsified for 3 min using a Kinematica Polytron 3100 rotor/stator at 10,000 rpm. The solution was further emulsified using a microfluidizer for 6 minutes. The methylene chloride was removed from the emulsion using a rotary evaporator (room temperature, 200 rpm, 3 min), resulting in an aqueous suspension of nanoparticles.

Light Scattering Analysis

The aqueous suspension of the Control 1 nanoparticles was filtered using a 1 μm glass membrane filter, diluted 1:10, and analyzed using DLS. The cumulant diameter of the nanoparticles in aqueous suspension was 115 nm, with a polydispersity of 0.31.

The aqueous suspension of Control 1 nanoparticles was allowed to stand unmixed at ambient conditions to measure stability. After 3 days, the nanoparticles began to agglomerate (visual observation). Optical microscopy showed many large drug crystals in the suspension. This comparison example shows that nanoparticles made with Eudragit RL alone do not provide a stable formulation.

Control 2

As a control, nanoparticles were prepared containing Drug 1 and the poorly aqueous soluble non-ionizable polymer ethylcellulose, but without an amine-functionalized methacrylate copolymer. To form Control 2 nanoparticles, 40.6 mg Drug 1 and 123.8 mg ethylcellulose were dissolved in 5 mL methylene chloride to form an organic solution. The organic solution was then poured into 20 mL deionized water, and emulsified using a Kinematica Polytron 3100 rotor/stator, and further emulsified using a Microfluidizer. The methylene chloride was removed from the emulsion using a rotary evaporator, resulting in an aqueous suspension of nanoparticles. The aqueous suspension was analyzed using DLS. The cumulant diameter of the nanoparticles was 815 nm, with a polydispersity of 0.41. Visual observation of the aqueous suspension confirmed large agglomerated and stringy material. These results show that nanoparticles made without an amine-functionalized methacrylate copolymer do not provide a stable formulation.

Example 3

Nanoparticles containing Drug 2 were prepared as follows. First, 1.1259 g Drug 2, 1.6875 g ethylcellulose, and 1.6875 g Eudragit RL PO were dissolved in 135 mL methylene chloride to form an organic solution. The organic solution was then poured into 450 mL deionized water and emulsified for 3 min using a Kinematica Polytron 3100 rotor/stator at 10,000 rpm. The solution was further emulsified using a microfluidizer, with an inlet pressure of 74 psi for 30 minutes. The methylene chloride was removed from the emulsion using a rotary evaporator (23° C., 200 rpm, 20 min), resulting in an aqueous suspension of nanoparticles.

Light Scattering Analysis

DLS analysis was performed on the nanoparticles of Example 3 as described above, and showed that the cumulant diameter of the nanoparticles in aqueous suspension was 127 nm, with a polydispersity of 0.18.

To measure nanoparticle potency, 100 μL of the aqueous suspension above was added to 1 mL methanol. The concentration of drug in solution was analyzed by HPLC using a Waters Symmetry $C_8$ column. The mobile phase consisted of 15% 0.2% $H_3PO_4$/85% methanol. UV absorbance was measured at 256 nm. The nanoparticle suspension was found to contain 2.9 mgA/mL Drug 2.

The aqueous suspension of nanoparticles was allowed to stand unmixed for 2 weeks (ambient conditions) to measure stability. DLS analysis showed that the cumulant diameter of the nanoparticle suspension after 2 weeks was 126 nm, with a polydispersity of 0.16. These results demonstrate that the nanoparticle suspension is stable for at least 2 weeks with no measurable particle agglomeration.

Free Drug Analysis

The amount of free drug provided by the nanoparticles of Example 3 was measured using nuclear magnetic resonance (NMR). For this test, a suspension containing 4.0 mg of the nanoparticles of Example 3 was added to Eppendorf tubes (in duplicate) containing 1.0 mL of deuterated PBS containing 29.2 mM sodium taurocholic acid (NaTC) and 5.6 mM of 1-palmitoyl-2-oleyl-sn-glycero-3-phosphocholine (POPC) (2 wt % NaTC/POPC). The solution also contained 0.11 mg 3-(trimethylsilyl)propionic-2,2,3,3-$d_4$ acid, sodium salt ("TSP"; a deuterated NMR reference standard). An internal standard solution of trifluoroacetic acid (TFA) was added to the tubes to give a concentration of 0.8976 mM $^{19}F$. After adding the deuterated NaTC/POPC solution, the tubes were vortexed 1 minute, and allowed to stand undisturbed for 6 hours in a 37° C. controlled temperature chamber. Prior to sampling, an aliquot was centrifuged to remove drug particulates. The supernatant was then carefully transferred to an 8 mm glass NMR tube. Crystalline Drug 2 alone was tested for comparison.

Fluorine spectra of the samples were recorded at 282.327 MHz on a Varian Gemini 2000, 300 MHz NMR equipped with a Nalorac 8 mm indirect detection probe. The sample temperature was maintained at 37° C. in the probe. Drug resonances were integrated relative to the internal standard peak and the drug concentration determined.

As shown in Table 3, the nanoparticle suspension of Example 3 provided a free drug concentration that was 3.1-fold the concentration of free drug provided by crystalline drug alone.

TABLE 3

| Suspension Sample | Free Drug (μg/mL) |
| --- | --- |
| Nanoparticles of Example 3 | 25 |
| Crystalline Drug 2 | 8 |

In Vivo Evaluation of the Nanoparticles of Example 3

The nanoparticles of Example 3 were evaluated in vivo. Samples were dosed orally as a suspension to 6 male beagle dogs. Animals were fasted overnight (14 to 15 hours predose) through at least 12 hours postdose. Approximately 50 mL of suspension (10 mgA/kg) was administered to each dog. The dose was administered via oral gavage, followed by approximately 5 mL water. Whole-blood samples (3-mL red-top Vacutainer tubes without serum separators) were taken from the jugular vein before dosing and at 0.25, 0.5, 1, 2, 3, 4, 5, 6, 8, 12, and 24 hours after dosing. Serum was harvested into tubes containing $K_2EDTA$ anticoagulant. Blood was maintained on wet ice prior to centrifugation to obtain plasma. Centrifugation began within 1 hour of collection, and samples were centrifuged at 2500 rpm for 15 minutes. Plasma was maintained on dry ice prior to storage at approximately −70° C. Plasma was analyzed using liquid chromatography with tandem mass spectrometry (LC/MS/MS). The results are shown in Table 4.

TABLE 4

| Parameter | Nanoparticles of Example 3 |
| --- | --- |
| $C_{max}$ (ng/mL) | 157 ± 44 |
| $T_{max}$ (hours) | 3 ± 1 |
| $AUC_{0-12\,hr}$ (ng/mL-hr) | 801 ± 274 |

Examples 4-7

Nanoparticles containing Drug 1 were prepared using various poorly aqueous soluble non-ionizable polymers and amine-functionalized methacrylate copolymer as listed in Table 5. The nanoparticles were made using the process described in Example 1, with the conditions shown in Table 6.

In all cases, the organic solvent was removed from the emulsion using a rotary evaporator, resulting in an aqueous suspension of nanoparticles.

TABLE 5

| Example | Drug 1 (wt %) | Non-ionizable Polymer | Amount (wt %) | Amine-functionalized methacrylate Copolymer | Amount (wt %) |
|---|---|---|---|---|---|
| 4 | 10 | Cellulose acetate | 55 | Eudragit RL PO | 35 |
| 5 | 25 | Cellulose acetate | 37.5 | Eudragit RL PO | 37.5 |
| 6 | 10 | Cellulose acetate butyrate | 55 | Eudragit RL PO | 35 |
| 7 | 25 | Cellulose acetate butyrate | 37.5 | Eudragit RL PO | 37.5 |

TABLE 6

| Item | Example 4 | Example 5 | Example 6 | Example 7 |
|---|---|---|---|---|
| Organic Solvent | Methylene Chloride | Methylene Chloride | Methylene Chloride | Methylene Chloride |
| Volume (mL) | 4 | 5 | 4 | 5 |
| Drug 1 (mg) | 20 | 20 | 20 | 20 |
| Non-ionizable Polymer (mg) | 110 | 60 | 110 | 60 |
| Amine-functionalized methacrylate Copolymer (mg) | 70 | 60 | 70 | 60 |
| Aqueous Volume (mL) | 20 | 20 | 20 | 20 |
| Emulsification Time (min) | 4 | 4 | 4 | 4 |
| Microfluidizer Pressure (psig) | 80 | 80 | 80 | 80 |
| Time (min) | 4 | 4 | 4 | 4 |

Light Scattering Analysis

The aqueous suspensions of Examples 4-7 were filtered using a 1 μm glass membrane filter, and analyzed using DLS as described above. The results are summarized in Table 7. The aqueous suspensions of nanoparticles were allowed to stand unmixed for the time shown in Table 7 at ambient conditions and the size determined again. These results are also shown in Table 7.

TABLE 7

| | Initial | | | After Storage | |
|---|---|---|---|---|---|
| Example | Diameter (nm) | Polydispersity | Storage Time (days) | Diameter (nm) | Polydispersity |
| 4 | 115 | 0.12 | 2 | 118 | 0.11 |
| 5 | 118 | 0.17 | 4 | 117 | 0.16 |
| 6 | 97 | 0.23 | 3 | 97 | 0.26 |
| 7 | 108 | 0.26 | 1 | 105 | 0.27 |

Example 8

Nanoparticles containing Drug 3 were prepared as follows. First, 298.7 mg Drug 3, 450.9 mg Ethocel, and 449.7 mg Eudragit RL were dissolved in 28 mL ethyl acetate and 6 mL methylene chloride to form an organic solution. The aqueous solution consisted of 68 mL deionized water. The organic solution was then poured into the aqueous solution and emulsified using high-shear mixing for 4 minutes, followed by high-pressure homogenization for 12 minutes. The solvents were removed from the emulsion using a rotary evaporator, resulting in an aqueous suspension of nanoparticles with a composition ratio of 25:37.5:37.5 Drug 3:Ethocel: EudragitRL. The average cumulant diameter was found to be 116 nm, with a polydispersity of 0.23.

To obtain the dried nanoparticle composition of Example 8, 1.4142 g PVP was added to the aqueous suspension above. The solution was frozen rapidly using liquid nitrogen, then lyophilized overnight to obtain a dry powder.

Nanoparticle Resuspension

The lyophilized nanoparticle composition of Example 8 was resuspended in aqueous solution. About 2 g of lyophilized nanoparticle composition was added to 10 mL of 20 mM phosphate buffer and sonicated about 2 minutes. Drops of the resuspended nanoparticle solution were added to deionized water in a cuvette, and particle size was analyzed using DLS as described above. The average cumulant diameter of the resuspended nanoparticles was 92 nm, with a polydispersity of 0.23. This demonstrates that a small particle size can be maintained after isolation of the nanoparticles in dry powder form, followed by resuspension.

The nanoparticle resuspension of Example 8 was allowed to stand unmixed for 1 week at ambient conditions to measure stability. DLS analysis showed that the average cumulant diameter of the nanoparticles in suspension after 1 week was 90 nm, with a polydispersity of 0.15. These results demonstrate that the nanoparticles of Example 8 in suspension were stable during storage with no significant particle agglomeration.

Example 9

Nanoparticles were made as described in Example 8, with the following exceptions. First, 89.9 mg Drug 3, 135.5 mg Ethocel, and 135.7 mg Eudragit RL were dissolved in 8 mL ethyl acetate and 2 mL methylene chloride to form an organic solution. The aqueous solution consisted of 20 mL deionized water. The organic solution was then poured into the aqueous solution and emulsified using high-shear mixing for 4 minutes, followed by high-pressure homogenization for 4 minutes. The solvents were removed, resulting in an aqueous suspension of nanoparticles with a composition ratio of 25:37.5:37.5 Drug 3:Ethocel:EudragitRL. The average cumulant diameter was found to be 113 nm, with a polydispersity of 0.21.

To obtain the dried nanoparticle composition of Example 9, 400 mg PVP was added to the aqueous suspension above. The solution was frozen rapidly using liquid nitrogen, then lyophilized overnight to obtain a dry powder.

Evaluation of Example 9 In Vivo

The nanoparticles of Example 9 were evaluated in vivo, in pigmented rabbits. The suspension was reconstituted by adding 1 mL deionized water to approximately 180 mg lyophilized nanoparticle composition and approximately 20 mg solid dextrose, to yield the nanoparticle suspension with an osmolarity of about 300 mOsm. The suspension was vortexed for 10 seconds following addition of resuspending media. Nanoparticle suspensions were then dosed topically as 50 μL eye drops, at a concentration of 20 mgA/mL.

Following administration of the eye drops, reduction in intraocular pressure was measured by tonometry. Drug 3 concentration was measured in the aqueous humor, iris ciliary body, and cornea. Control 3 consisted of Drug 3 in the form of milled crystals with mean particle size between 200 and 10,000 nm. The data are shown in Table 8.

TABLE 8

| Time post dose (hr) | IOP lowering (mm Hg) | | Concentration in AH (ng/ml) | | Concentration in ICB (ng/g) | | Concentration in Cornea (ng/g) | |
|---|---|---|---|---|---|---|---|---|
| | Example 9 | Control 3 | Example 9 | Control 3 | Example 9 | Control 3 | Example 9 | Control 3 |
| 0 | 0 | 0 | | | | | | |
| 0.5 | | | 1079 | 95 | 1268 | 238 | 15221 | 2571 |
| 1 | −1.46 | −0.23 | 1175 | 196 | 1051 | 194 | 7842 | 1904 |
| 2 | −5.19 | 0.79 | | | | | | |
| 3 | | | 1378 | 206 | 1181 | 465 | 5789 | 1577 |
| 4 | −3.77 | 0.63 | | | | | | |
| 6 | −2.90 | −0.52 | 164 | 17 | 438 | 160 | 1360 | 332 |

("IOP" means intra-ocular pressure; "AH" means aqueous humor; and "ICB" means iris-ciliary body.)

The data in Table 8 show improved efficacy obtained using nanoparticles of the invention.

Example 10

Nanoparticles were made containing Drug 4. The nanoparticles of Example 10 were prepared as follows. First, 90 mg Drug 4, 139 mg Ethocel, and 135 mg Eudragit RL were dissolved in 5 mL methylene chloride to form an organic solution. The aqueous solution consisted of 20 mL deionized water. The organic solution was then poured into the aqueous solution and emulsified using high-shear mixing for 4 minutes, followed by high-pressure homogenization for 4 minutes. The solvents were removed from the emulsion using a rotary evaporator, resulting in an aqueous suspension of nanoparticles with a composition ratio of 25:37.5:37.5 Drug 4:Ethocel:Eudragit RL. The average cumulant diameter was found to be 115 nm, with a polydispersity of 0.184.

To obtain the dried nanoparticle composition of Example 10, 372 mg PVP was added to the aqueous suspension above. The solution was frozen rapidly using liquid nitrogen, then lyophilized overnight to obtain a dry powder.

Evaluation of Example 10 In Vivo

The nanoparticles of Example 10 were evaluated in vivo, in pigmented rabbits. The suspension was reconstituted by adding 1 mL deionized water to approximately 195 mg lyophilized nanoparticle composition and approximately 20 mg solid dextrose, to yield the nanoparticle suspension with an osmolarity of about 300 mOsm. The suspension was vortexed for 10 seconds following addition of resuspending media. Nanoparticle suspensions were then dosed topically as 50 μL eye drops, at a concentration of 20 mgA/mL.

Following administration of the eye drops, reduction in intraocular pressure was measured by tonometry. The data are shown in Table 9.

TABLE 9

| Time post dose (hr) | IOP lowering (mm Hg) |
|---|---|
| 0 | 0 |
| 1 | −1.52 |
| 2 | −1.00 |
| 3 | −0.71 |
| 4 | −0.58 |

The data in Table 9 show IOP lowering for the nanoparticles of Example 12 in pigmented rabbits following a single solution dose.

Example 11

Nanoparticles containing brinzolamide (Drug 5) were prepared as follows. First, 400 mg Drug 5, 904.7 mg Ethocel, and 701.4 mg Eudragit RL were dissolved in 16 mL ethyl acetate and 4 mL methylene chloride to form an organic solution. The aqueous solution consisted of 40 mL deionized water. The organic solution was then poured into the aqueous solution and emulsified using high-shear mixing for 5 minutes, followed by high-pressure homogenization for 8 minutes. The solvents were removed from the emulsion using a rotary evaporator, resulting in an aqueous suspension of nanoparticles with a composition ratio of 20:45:35 Drug 5:Ethocel:EudragitRL. The average cumulant diameter was found to be 104 nm, with a polydispersity of 0.22.

To obtain the dried nanoparticles of Example 11, 1.6 g PVP was added to the aqueous suspension above. The solution was frozen rapidly using liquid nitrogen, then lyophilized overnight to obtain a dry powder.

Nanoparticle Resuspension

The lyophilized nanoparticle composition of Example 11 was resuspended in deionized water. About 165 mg of lyophilized nanoparticle composition and 54 mg dextrose were added to 1.5 mL of water in an HPLC vial, and the vial was shaken by hand. Drops of the resuspended nanoparticle solution were added to deionized water in a cuvette, and particle size was analyzed using DLS as described above. The average cumulant diameter of the resuspended nanoparticles was 103 nm, with a polydispersity of 0.22.

Evaluation of Example 11 In Vivo

The resuspended nanoparticles of Example 13 were tested in vivo. Example 11 nanoparticles were compared to a commercial Azopt formulation in normotensive pigmented rabbits, with a single topical dose. Following administration of the eye drops, reduction in intraocular pressure was measured by tonometry. The data are shown in Table 10.

TABLE 10

| | IOP lowering (mm Hg) | |
|---|---|---|
| Time post dose (hr) | Example 11 | Azopt commercial formulation |
| 0 | 0 | 0 |
| 1 | −1.96 | −1.86 |
| 2 | −2.02 | −2.43 |
| 3 | −1.77 | −1.45 |
| 4 | −2.27 | −1.38 |
| 6 | −1.42 | −0.24 |
| 8 | −1.71 | −0.1 |

The data in Table 10 show improved lowering of intraocular pressure from 3 to 8 hours compared to the commercial formulation, resulting in improved treatment efficacy.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A pharmaceutical composition comprising nanoparticles, said nanoparticles consisting of:
(a) a poorly water soluble drug having a solubility in water of less than 5 mg/mL over the pH range of 6.5 to 7.5 at 25° C., at least 90 wt % of said drug in said nanoparticles being non-crystalline;
(b) a poorly aqueous soluble non-ionizable polymer selected from the group consisting of ethylcellulose, cellulose acetate, cellulose propionate, cellulose butyrate, and cellulose acetate butyrate; and
(c) an amine-functionalized methacrylate copolymer;
wherein said nanoparticles comprise a core and said core comprises said drug and said non-ionizable polymer; wherein said nanoparticles have an average diameter of less than 500 nm; and said drug, said non-ionizable polymer, and said amine-functionalized methacrylate copolymer collectively constitute at least 80 wt % of said nanoparticles.

2. The composition of claim 1 wherein said core further comprises said amine-functionalized methacrylate copolymer.

3. The composition of claim 1 wherein said drug, said non-ionizable polymer, and said amine-functionalized methacrylate copolymer collectively constitute at least 90 wt % of said nanoparticles.

4. The composition of claim 1 wherein said nanoparticles consist essentially of said drug, said non-ionizable polymer, and said amine-functionalized methacrylate copolymer.

5. The composition of claim 1 wherein said nanoparticles have the following composition: from 5 to 60 wt % of said drug, from 10 to 75 wt % of said non-ionizable polymer, and from 5 to 60 wt % of said amine-functionalized methacrylate copolymer.

6. The composition of claim 1 wherein said nanoparticles have an average diameter of less than 300 nm.

7. The composition of claim 1 wherein said amine-functionalized methacrylate copolymer is poly[ethylacrylate-co-methyl methacrylate-co-trimethylamonioethyl methacrylate chloride].

8. The composition of claim 1 further comprising water, wherein said nanoparticles are suspended in said water.

9. A process for forming nanoparticles, comprising the steps:
(a) forming an organic solution comprising a poorly water soluble drug and a poorly aqueous soluble non-ionizable polymer selected from the group consisting of ethylcellulose, cellulose acetate, cellulose propionate, cellulose butyrate, and cellulose acetate butyrate, the non-ionizable polymer dissolved in a solvent, wherein said drug has a solubility in water of less than 5 mg/ml over the pH range of 6.5 to 7.5 at 25° C.;
(b) forming an aqueous solution, wherein said drug and said non-ionizable polymer are poorly soluble in said aqueous solution;
(c) adding an amine-functionalized methacrylate copolymer to at least one of said organic solution and said aqueous solution;
(d) mixing said organic solution with said aqueous solution to form a first mixture;
(e) removing said solvent from said first mixture to form a suspension comprising said nanoparticles and said aqueous solution, wherein
(i) said nanoparticles have an average diameter of less than 500 nm;
(ii) at least 90 wt % of said drug in said nanoparticles is noncrystalline; and
(iii) said drug, said non-ionizable polymer, and said amine-functionalized methacrylate copolymer collectively constitute at least 80 wt % of said nanoparticles.

10. The process of claim 9 further comprising the additional step of
(f) adding a matrix material to said suspension.

11. The process of claim 10 wherein said matrix material is selected from the group consisting of polyvinylpyrrolidone, trehalose, hydroxypropyl methyl cellulose, hydroxypropyl cellulose, casein, caseinate, albumin, gelatin, acacia, lactose, mannitol, pharmaceutically acceptable forms thereof, and mixtures thereof.

12. The process of claim 10 further comprising the additional step of
(g) removing liquid from said suspension to form a solid composition comprising said nanoparticles.

13. The process of claim 12 wherein said liquid is removed by one or more processes selected from the group consisting of spray drying, spray coating, spray layering, lyophilization, evaporation, vacuum evaporation, and filtration.

14. The process of claim 13 wherein said liquid is removed by spray drying.

15. The process of claim 13 wherein said liquid is removed by lyophylization.

16. A pharmaceutical composition comprising nanoparticles, said nanoparticles comprising:

(a) a poorly water soluble drug having a solubility in water of less than 5 mg/mL over the pH range of 6.5 to 7.5 at 25° C., at least 90 wt % of said drug in said nanoparticles being non-crystalline;
(b) a poorly aqueous soluble non-ionizable polymer selected from the group consisting of ethylcellulose, cellulose acetate, cellulose propionate, cellulose butyrate, and cellulose acetate butyrate; and
(c) an amine-functionalized methacrylate copolymer;
wherein said nanoparticles comprise a core and said core comprises said drug and said non-ionizable polymer; wherein said nanoparticles have an average diameter of less than 500 nm; and said drug, said non-ionizable polymer, and said amine-functionalized methacrylate copolymer collectively constitute at least 80 wt % of said nanoparticles.

* * * * *